United States Patent [19]

Vorbrüggen et al.

[11] Patent Number: 4,489,092
[45] Date of Patent: Dec. 18, 1984

[54] PROSTANOIC ACID DERIVATIVES AND THEIR PREPARATION

[75] Inventors: Helmut Vorbrüggen; Norbert Schwarz; Olaf Loge; Walter Elger, all of Berlin, Fed. Rep. of Germany

[73] Assignee: Schering Aktiengesellschaft, Bergkamen and Berlin, Fed. Rep. of Germany

[21] Appl. No.: 413,940

[22] Filed: Sep. 1, 1982

Related U.S. Application Data

[60] Division of Ser. No. 256,369, Apr. 22, 1981, Pat. No. 4,359,467, which is a division of Ser. No. 069,193, Aug. 24, 1970, Pat. No. 4,284,646, which is a continuation of Ser. No. 932,823, Aug. 10, 1978, abandoned, which is a continuation-in-part of Ser. No. 821,130, Aug. 2, 1977, abandoned.

[30] Foreign Application Priority Data

Aug. 6, 1976 [DE] Fed. Rep. of Germany ....... 2635985

[51] Int. Cl.³ .................. C07C 177/00; A61K 31/557
[52] U.S. Cl. .................. 424/304; 260/345.7 P; 260/345.8 P; 260/347.3; 260/347.4; 260/456 R; 260/464; 260/340.5 P; 260/340.7; 260/340.9 P; 260/410; 542/426; 556/441; 424/278; 424/305; 424/317; 560/118; 560/121; 560/231; 562/500; 562/503
[58] Field of Search .............. 560/121, 118, 231; 562/503, 500; 424/305, 278, 317, 304; 260/345.7 P, 345.8 P, 347.3, 347.4, 456 R, 464, 340.5 P, 340.7, 340.9 P, 410; 542/426; 556/441

[56] References Cited

U.S. PATENT DOCUMENTS 3,932,479  1/1976  Floyd ............................ 260/448
4,220,798  9/1980  Scolastico ....................... 560/121

Primary Examiner—Robert Gerstl
Attorney, Agent, or Firm—Millen & White

[57] ABSTRACT

Prostanoic acid derivatives of the formula

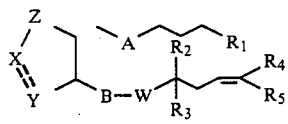

wherein $R_1$ is an acid, ester, amide or hydroxyalkylene group; $R_2$ and $R_3$ are H or alkyl; $R_4$ and $R_5$ are both $CH_3$ or one is Cl and the other is $CH_3$; A is $CH_2CH_2$ or $-CH=CH$; B is $CH_2CH_2$, trans-$CH=CH$, $-C\equiv C-$ or

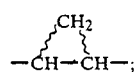

W is free or functionally modified hydroxyalkylene or carbonyl; Z is free or functionally modified hydroxymethylene or carbonyl; X — Y is either

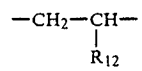

or, when Z is free or functionally modified hydroxymethylene,

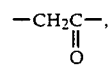

or, when Z is free or functionally modified carbonyl, $-CH=CH-$, $R_{12}$ being H, $CH_3$, CH or free or functionally modified hydroxy; and physiologically acceptable salts thereof when $R_1$ is an acid group, possess pharmacological activity, including abortion triggering activity.

38 Claims, No Drawings

PROSTANOIC ACID DERIVATIVES AND THEIR PREPARATION

This is a division, of application Ser. No. 256,369 of Apr. 22, 1981 U.S. Pat. No. 4,359,467; which is a division of Ser. No. 069,193 of Aug. 24, 1970 U.S. Pat. No. 4,284,646; which is a continuation of Ser. No. 932,823 of Aug. 10, 1978 abandoned; which is a continuation-in-part of 821,130 of Aug. 2, 1977, now abandoned.

BACKGROUND OF THE INVENTION

This invention relates to novel prostanoic acid derivatives and to processes for their production and use.

SUMMARY OF THE INVENTION

In a composition aspect, this invention relates to novel prostanoic acid derivatives of general Formula I

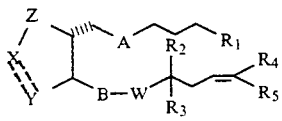

wherein $R_1$ is

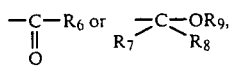

wherein $R_6$ is hydroxy; a straight-chain or branched alkoxy of 1–10 carbon atoms; aryloxy; O—CH$_2$—U—V wherein U is a direct bond, carbonyl or carbonyloxy and V is a phenyl ring substituted by one or more of phenyl, alkoxy of 1–2 carbon atoms, or halogen atoms, preferably bromine atoms; or —NHR$_{10}$ wherein R$_{10}$ is alkyl, aryl or the acyl radical of an organic carboxylic or sulfonic acid of 1–15 carbon atoms; and wherein R$_7$ and R$_8$ each are hydrogen atoms or alkyl of 1–4 carbon atoms and R$_9$ is the acyl radical of an organic carboxylic or sulfonic acid of 1–15 carbon atoms or of an inorganic acid or is

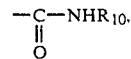

R$_{10}$ having the values given above; A is —CH$_2$—CH$_2$— or cis- or trans-CH=CH—; B is —CH$_2$—CH$_2$—, trans-CH=CH—, —C≡C— or

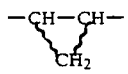

wherein the methylene group can be in the α- or β-position; W is free or functionally modified hydroxymethylene, a free or functionally modified carbonyl, or

wherein $R_{11}$ is alkyl of 1–5 carbon atoms and the OH-group can be in the α- or β-position and can be functionally modified; Z is carbonyl or hydroxymethylene, either of which can be free or functionally modified; X⎯⎯⎯Y is either

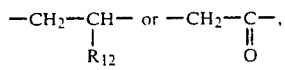

when Z is a free or functionally modified hydroxymethylene group, or is either

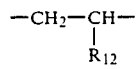

or —CH=CH—, when Z is a free or functionally modified carbonyl group, wherein $R_{12}$ is a hydrogen atom, methyl, a cyanide group (—CN), or a free or functionally modified hydroxy; $R_2$ is a hydrogen atom or alkyl; $R_3$ is a hydrogen atom or alkyl; $R_4$ and $R_5$ each are methyl or one of $R_4$ and $R_5$ is a chlorine atom and the other is methyl; and, when $R_6$ is hydroxy, the physiologically acceptable salts thereof with bases.

In another composition aspect, this invention relates to pharmaceutical compositions comprising a novel compound of this invention.

In process aspects, this invention relates to methods of making and using the novel compounds of this invention.

DETAILED DISCUSSION

Contemplated classes of compounds within the scope of Formula I include those wherein:

(a) $R_6$ is OH;
(b) $R_6$ is alkoxy;
(c) $R_6$ is aryloxy;
(d) $R_6$ is —O—CH$_2$—V;
(e) $R_6$ is

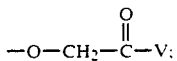

(f) $R_6$ is

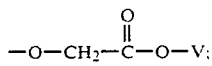

(g) $R_6$ is —NH—alkyl;
(h) $R_6$ is —NH—aryl;
(i) $R_6$ is —NH—acyl;
(j) B is —CH$_2$CH$_2$ or trans-CH=CH—, including those of each of (a) through (i);
(k) B is —C≡C—, including those of each of (a) through (i);
(l) B is

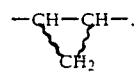

including those of each of (a) through (i);
(m) W is hydroxymethylene, including those of each of (a) through (l);
(n) W is alkoxymethylene, including those of each of (a) through (l);

(o) W is acyloxymethylene, including those of each of (a) through (l);

(p) W is carbonyl, including those of each of (a) through (l);

(q) W is dialkyl ketalized carbonyl, including those of each of (a) through (l);

(r) W is arylenedioxy ketalized carbonyl, including those of each of (a) through (l);

(s) W is alkylenedioxy ketalized carbonyl, including those of each of (a) through (l);

(t) Z is carbonyl, including those of each of (a) through (s);

(u) Z is dialkyl ketalized carbonyl, including those of each of (a) through (s);

(v) Z is arylenedioxy ketalized carbonyl, including those of each of (a) through (s);

(w) Z is alkylenedioxy ketalized carbonyl, including those of each of (a) through (s);

(x) Z is hydroxymethylene, including those of each of (a) through (s);

(y) Z is esterified hydroxymethylene, including those of each of (a) through (s);

(z) Z is etherified hydroxymethylene, including those of each of (a) through (s);

(aa) $X\text{------}Y$ is $-CH_2CH_2-$, including those of each of (a) through (z);

(bb) $X\text{------}Y$ is $-CH_2CHOH-$, including those of each of (a) through (z);

(cc) $X\text{------}Y$ is $-CH_2CHCN-$, including those of each of (a) through (z);

(dd) $X\text{------}Y$ is $-CH_2CCH_3-$, including those of each of (a) through (z);

(ee) $X\text{------}Y$ is $-CH_2-CO-$, including those of each of (a) through (z);

(ff) both $R_4$ and $R_5$ are $CH_3$, including those of each of (a) through (ee); and (gg) one of $R_4$ and $R_5$ is Cl, including those of each of (a) through (ee).

Examples of alkyl groups $R_2$ and $R_3$ are straight-chain and branched alkyl residues of 1-5 carbon atoms, such as, for example, methyl, ethyl, propyl, isopropyl, butyl, isobutyl, and pentyl. Preferred are the methyl and ethyl groups.

Examples of substituted or unsubstituted aryloxy groups $R_6$ are phenoxy, 1-naphthoxy, and 2-naphthoxy, each of which can be substituted by 1-3 halogen atoms, one phenyl group, one to three alkyl groups of respectively 1-4 carbon atoms, one chloromethyl, fluoromethyl, trifluoromethyl, carboxyl or hydroxy group.

Examples of alkoxy groups $R_6$ are straight-chain and branched-chain, saturated and unsaturated alkoxy residues, preferably those which are saturated and contain 1-10, especially 1-6 carbon atoms. Examples in this connection are methoxy, ethoxy, propoxy, butoxy, isobutoxy, tert.-butoxy, pentoxy, hexoxy, heptoxy, octoxy, butenyloxy, isobutenyloxy, propenyloxy.

For the salt formation, all inorganic and organic bases can be utilized, as they are known to those skilled in the art for the preparation of physiologically compatible salts. Examples are alkali hydroxides, such as sodium or potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine.

Examples of alkyl groups $R_{10}$ are straight-chain or branched alkyl groups of 1-10 carbon atoms, such as, for example, methyl, ethyl, propyl, isobutyl, butyl, pentyl, heptyl, hexyl, decyl, and cycloalkyl groups of 3-8 carbon atoms.

The alkyl groups $R_{10}$ can optionally be mono- or polysubstituted by halogen atoms, alkoxy groups, optionally substituted aryl groups, dialkyl amines, and trialkyl ammonium.

Examples of substituents are fluorine, chlorine or bromine atoms, phenyl, dimethylamine, diethylamine, methoxy, ethoxy.

Preferred alkyl groups $R_{10}$ are methyl, ethyl, propyl, isobutyl, butyl, trichloromethyl and trifluoromethyl.

Cycloalkyl groups $R_{10}$ are those of 3-8 carbon atoms, such as, for example, cyclopropyl, cyclobutyl, cyclopentyl, cyclohexyl preferably cyclopropyl.

Examples of aryl groups $R_{10}$ are substituted as well as unsubstituted aryl groups and heteroaryl groups, such as, for example, phenyl, 1-naphthyl, and 2-naphthyl, each of which can be substituted by 1-3 halogen atoms, one phenyl group, one to three alkyl groups of respectively 1-4 carbon atoms, a chloromethyl, fluoromethyl, trifluoromethyl or alkoxy group; and thienyl, furyl or pyridyl. The substitution in the 3- and 4-positions on the phenyl ring is preferred, for example, by fluorine, chlorine, alkoxy or trifluoromethyl.

Suitable acyl residues $R_9$ and $R_{10}$, respectively, are physiologically compatible acyl residues, e.g., of organic carboxylic acids and sulfonic acids of 1-15 carbon atoms pertaining to the aliphatic, cycloaliphatic, aromatic, aromatic-aliphatic, or heterocyclic series. These acids can be saturated, unsaturated and/or polybasic and/or substituted in the usual manner. Examples of substituents are alkyl, hydroxy, alkoxy, oxo or amino groups, or halogen atoms.

The following carboxylic acids are illustrative: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di-, and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid. Especially preferred acyl residues are those of up to 10 carbon atoms.

Examples of sulfonic acids are methanesulfonic acid, trifluoromethanesulfonic acid, ethanesulfonic acid, isopropylsulfonic acid, β-chloroethanesulfonic acid, butanesulfonic acid, cyclopropanesulfonic acid, cyclopentanesulfonic acid, cyclohexanesulfonic acid, benzenesulfonic acid, p-toluenesulfonic acid, p-chlorobenzenesulfonic acid, p-methoxybenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, thiopheno-, and morpholinosulfonic acids.

Also suitable for $R_9$ are the customary inorganic acids, e.g. sulfuric acid and phosphoric acid.

Examples of alkyl groups $R_7$ and $R_8$ are straight-chain and branched alkyl residues of 1-4 carbon atoms, for example the methyl, ethyl, propyl, isopropyl, butyl, isobutyl, and tert.-butyl residues. The methyl and ethyl groups are preferred.

The hydroxy groups $R_{12}$ and those in W and Z can be functionally modified, for example by etherification or esterification, wherein the free or modified hydroxy groups in W and Z can be in the α or β-position.

Suitable ether and acyl residues are those known to persons skilled in the art. Readily cleavable ether residues are preferred, such as, for example, the tetrahydropyranyl, tetrahydrofuranyl, α-ethoxyethyl, trimethylsilyl, dimethyl-tert.-butylsily, and tri-p-benzylsilyl residues.

Suitable acyl residues are the same as set forth for $R_9$ e.g., acetyl, propionyl, butyryl, and benzoyl.

If W and/or Z represent a carbonyl group, the latter can be functionally modified in accordance with methods known to those skilled in the art, for example by ketalizing. Especially advantageous is the preparation of cyclic ketals, e.g., with ethylene glycol, 1,3-propanediol, 2,2-dimethyl-1,3-propanediol, 1,2-cyclopentanediol, or glycerol.

Examples of alkyl groups $R_{11}$ are straight-chain and branched-chain alkyl residues of 1-5 carbon atoms, such as, for example, the methyl, ethyl, propyl, isopropyl, butyl, isobutyl, tert.-butyl, and pentyl residues. The methyl and ethyl groups are preferred.

In a process aspect, this invention relates to a process for the preparation of the novel prostanoic acid derivatives of general Formula I, characterized in that, in a conventional manner (a) a lactol of general Formula II

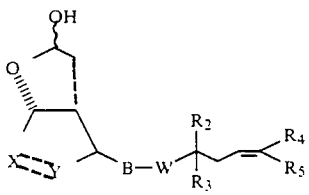

II wherein
$R_2$, $R_3$, $R_4$, $R_5$, B, W, and 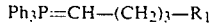 have the above-indicated meanings and
free hydroxy groups are optionally protected intermediarily,
is reacted with a compound of general Formula III $$Ph_3P=CH-(CH_2)_3-R_1$$ III wherein
Ph represents a phenyl group and
$R_1$ has the above-indicated meanings;
or
(b) an aldehyde of general Formula IV

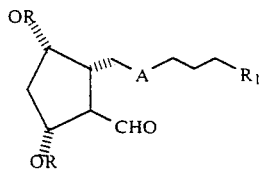

IV wherein
A and $R_1$ have the above-indicated meanings and
R represents an ether or acyl residue, is reacted with a compound of general Formula Va or Vb

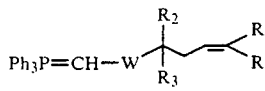

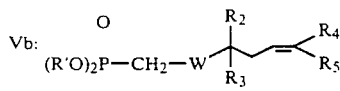

wherein Ph, W, $R_2$, $R_3$, $R_4$, and $R_5$ have the above-indicated meanings, and R' represents a lower alkyl group, and optionally subsequently, in any desired sequence, a carbonyl group in $R_1$ is esterified or converted into a

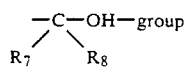

and the latter is then esterified and/or free hydroxy groups are oxidized and/or a 9-keto group is reduced and/or a 9-keto compound is dehydrated under elimination of the 11-hydroxy group and/or a 10,11-double bond is converted into an 11-cyano or 11-alkyl group and/or a 13,14- or 10,11-double bond is hydrogenated and/or a methylene group is introduced at the 13,14-double bond and/or free keto groups are ketalized and-/or functionally modified hydroxy groups are liberated; and optionally a 1-carboxy compound is converted with a base into a physiologically compatible salt and the racemates are separated, if necessary.

The reaction of the lactols II with the phosphoranes of general Formula III and the reaction of the aldehydes IV with the phosphoranes of general Formula V are conducted in accordance with conventional methods at temperatures of 0° C. to 100° C., preferably at 20°-80° C., in an aprotic solvent, such as, for example, dimethyl sulfoxide, dimethylformamide, benzene, toluene, xylene, diethyl ether, tetrahydrofuran, dioxane, chloroform and methylene chloride.

The introduction of the ester group into $R_1$ wherein $R_6$ represents an alkoxy group of 1-10 carbon atoms, takes place according to methods known to those skilled in the art. The 1-carboxy compounds are reacted, for example, with diazohydrocarbons in a conventional manner. The esterification with diazohydrocarbons takes place, for example, by mixing a solution of the diazohydrocarbon in an inert solvent, preferably in diethyl ether, with the 1-carboxy compound in the same or another inert solvent, e.g. methylene chloride. After the reaction is finished within one to 30 minutes, the solvent is removed and the ester is purified in the usual way.

Diazoalkanes are either known or can be prepared according to conventional methods [Org. Reactions 8: 389-394 (1954)].

To introduce the ester group into $R_1$ wherein $R_6$ is a substituted or unsubstituted aryloxy group, the 1-carboxy compounds are reacted with the corresponding aryl hydroxy compounds with dicyclohexylcarbodiimide in the presence of a suitable base, e.g., pyridine or triethylamine, in an inert solvent. Suitable solvents are methylene chloride, ethylene chloride, chloroform, ethyl acetate, tetrahydrofuran, preferably chloroform.

The reaction is conducted at temperatures of between −30° C. and +50° C., preferably at 10° C.

To introduce the ester group into $R_1$ wherein $R_6$ is an O—CH$_2$—U—V group, the 1-carboxy compound of general Formula I is reacted, in the presence of an agent splitting off hydrogen halide, with a halogen compound of the general formula Hal—CH$_2$—U—V wherein
Hal is a halogen atom, preferably bromine,
U is a direct bond or a carbonyl or carbonyloxy group, and
V is a phenyl ring substituted by one or more phenyl groups, alkoxy groups of 1–2 carbon atoms, or halogen atoms, preferably bromine atoms.

Examples of agents splitting off hydrogen halide are silver oxide, sodium carbonate, potassium carbonate, sodium bicarbonate, potassium bicarbonate, or amines, such as trimethylamine, triethylamine, tributylamine, trioctylamine, and pyridine. The reaction with the halogen compound is conducted in an inert solvent, preferably in acetone, acetonitrile, dimethylacetamide, dimethylformamide, or dimethyl sulfoxide, at temperatures of −80° to +100° C., preferably at room temperature.

The introduction of a

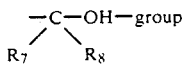

into $R_1$ takes place in accordance with conventional methods, such as, for example, if $R_7$ and $R_8$ represent hydrogen atoms, by reducing the prostanoic acid esters with lithium aluminum hydride. If $R_7$ is a hydrogen atom and $R_8$ is an alkyl group, it is possible, for example, to reduce the prostanoic acid derivative with diisobutyl aluminum hydride to the aldehyde and then react the latter with alkyl lithium. If $R_7$ and $R_8$ represent alkyl groups, the reduction to the alcohol is usually carried out by reacting a prostanoic acid ester with alkyl lithium.

The subsequent esterification of the alcohols takes place conventionally, for example by reacting a 1-alcohol with an acid derivative, e.g., an acid halogenide, in the presence of a base, such as, for example, triethylamine or, when $R_9$ is a

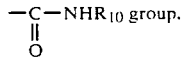

by reacting a 1-alcohol with an isocyanate according to conventional methods.
A

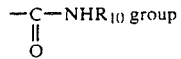

can be prepared according to conventional methods, for example by reacting a prostaglandin acid with an isocyanate.

The oxidation of any hydroxy groups present is effected by the use of conventional methods with the customary oxidizing agents. For example, the oxidation of the 9-hydroxy group can be accomplished by introducing the silyl group (Chem. Comm. 1972: 1120) with Jones reagent while intermediarily blocking the 11- and 15-hydroxy groups.

The reduction of the 9-keto group to produce the corresponding 9β-hydroxy compounds takes place with a reducing agent suitable for the reduction of ketones, such as, for example, sodium borohydride or zinc borohydride. The thus-obtained mixture of epimers is separated, for example, in the usual way by column chromatography or layer chromatography.

The dehydration of the 9-oxo compound wherein the 11-hydroxy group is split off, along with a hydrogen atom from the 10-position, thus obtaining a prostaglandin A derivative, can be carried out under conditions generally known to those skilled in the art. In general, the dehydration takes place in a solution of an organic acid, such as acetic acid, or an inorganic acid, such as hydrochloric acid, or in an acetic anhydridepyridine mixture at temperatures between 20° and 80° C.

The substitution of the 10,11-double bond takes place according to the usual methods, for example, in order to introduce an 11-cyano group, by reacting a prostaglandin A derivative with acetone cyanohydrin in the presence of a base and, in order to introduce an 11-alkyl group, for example by reacting a prostaglandin A derivative with a dialkyl copper lithium reagent.

If C═C-double bonds present in the primary product are to be reduced, the hydrogenation is conducted according to known methods. Thus, for example, the 10,11-double bond is hydrogenated, with simultaneous reduction of the 9-keto group, in a selective fashion with sodium borohydride.

The hydrogenation of the 13,14-double bond can be effected according to the methods well-known to those skilled in the art, for example by reacting a 13,14- and 18,19-unsaturated 15-ketoprostanoic acid with sodium borohydride in alcohol and then isolating an 18,19-unsaturated 15-hydroxyprostanoic acid.

The introduction of methylene into the 13,14-double bond is conducted as usual with diazomethane in an inert solvent, such as diethyl ether, tetrahydrofuran, dioxane, methylene chloride, chloroform, benzene, toluene, in the presence of noble metal salts, preferably palladium(II) acetate, at temperatures of between −100° and +80° C., preferably at −10° to +30° C. During this reaction, a mixture of the readily separable 13α,14α-methylene compound and of the 13β,14β-methylene compound is produced. The separation of the less polar 13α,14α-methylene compound from the more polar 13β,14β-methylene compound can be accomplished by usual methods, such as chromatography and/or fractional crystallization.

The ketalization of the 9- or 15-carbonyl group takes place in the usual way. For example, it is possible to conduct a heating step with ethylene glycol in the presence of an acidic catalyst, with water being split off. Especially suitable acidic catalysts are p-toluenesulfonic acid and perchloric acid.

The liberation of the functionally modified hydroxy groups take place according to known methods. For example, hydroxy blocking groups, e.g., a tetrahydropyranyl radical, are split off in an aqueous solution of an organic acid, such as, for example, oxalic acid, acetic acid, propionic acid, and others; or in an aqueous solution of an inorganic acid, e.g. hydrochloric acid. To improve solubility, a water-miscible, inert organic solvent is suitably added. Suitable organic solvents are, for example, alcohols, such as methanol and ethanol, ethers, such as dimethoxyethane, dioxane, and tetrahydrofuran, and acetone. Tetrahydrofuran is preferably employed. The splitting off step is preferably conducted at temperatures of between 20° and 80° C.

The saponification of the acyl groups is conducted, for example, with alkali or alkaline earth carbonates or hydroxides in an alcohol or in the aqueous solution of an alcohol. Suitable alcohols are aliphatic alcohols, e.g., methanol, ethanol, butanol, and so on, preferably methanol. Suitable alkali carbonates and hydroxides are potassium and sodium salts, the potassium salts being preferred. Examples of suitable alkaline earth carbonates and hydroxides are calcium carbonate, calcium hydroxide, and barium carbonate. The reaction takes place at −10° to +70° C., preferably at +25° C.

The prostaglandin derivatives of general Formula I wherein $R_1$ is a carboxy group can be converted into salts with suitable amounts of the corresponding inorganic bases, under neutralization. For example, when dissolving the corresponding PG acids in water containing the stoichiometric amount of the base, the solid inorganic salt is obtained after evaporation of the water or after the addition of a water-miscible solvent, such as, for example, alcohol or acetone.

To produce an amine salt, this process being conducted in the usual manner, the PG acid is dissolved, for instance, in a suitable solvent, for example ethanol, acetone, diethyl ether, or benzene, and at least the stoichiometric amount of the amine is added to this solution. During this step, the salt is ordinarily obtained in the solid phase, or it is isolated as usual after evaporation of the solvent.

The separation of the racemates takes place according to conventional methods, such as by salt formation with the aid of an optically active base, for example dehydroabietylamine, amphetamine, quinine, and others.

The novel prostanoic acid derivatives of general Formula I are valuable pharmaceuticals, since they exhibit, with a similar spectrum of activity, a substantially stronger activity and a substantially longer period of effectiveness than the corresponding natural prostaglandins.

The novel prostaglandin analogs of the F-, E, and D-type have a very strong uterus-contracting effect and furthermore act luteolytically, i.e., for triggering abortion smaller doses are necessary than in case of the corresponding natural prostaglandins.

In recording the isotonic uterus contraction on narcotized rats and on the isolated rat uterus, it is found that the compounds of this invention are substantially more effective and the durations of activity last longer than in case of the natural prostaglandins.

The novel prostanoic acid derivatives are suitable, after a one-time intrauterine administration, to induce menstruation or to interrupt a pregnancy. They are furthermore suitable for synchronizing the sexual cycle in female mammals, such as monkeys, cattle, pigs, etc.

The high dissociation of activity of the compounds according to the present invention is demonstrated when tested on other smooth-muscular organs, such as, for example, on the guinea pig ileum or on the isolated rabbit trachea, where a substantially lower stimulation can be observed than is the case when utilizing the natural prostaglandins.

The active agents of this invention pertaining to the PGE series show, on the isolated rabbit trachea in vitro, a bronchodilatory activity and strongly inhibit gastric acid secretion; furthermore, they have a regulating effect on cardiac dysrhythmia. The novel compounds of the PGA and PGE series also lower the blood pressure and have a diuretic effect.

The active agents of this invention pertaining to the F series have a lower bronchoconstrictive effect than natural prostaglandin $F_{2\alpha}$, which is of great advantage for their therapeutic use.

For medical application, the active agents can be converted into a form suitable for inhalation, for oral administration, or for parenteral application.

For inhalation purposes, aerosol or spray solutions are suitable.

For oral application, tablets, dragees, or capsules are advantageous.

For parenteral administration, sterile, injectable, aqueous or oily solutions can be used.

Consequently, the invention also relates to medicinal agents on the basis of the compounds of general Formula I and customary auxiliary agents and vehicles.

The active agents of this invention are to serve, in conjunction with the auxiliary substances known and customary in galenic pharmacy, for example, for the production of preparations to trigger abortion, to control the cycle, or to induce labor. For this purpose, it is possible to employ sterile, aqueous solutions containing 0.01–10 μg./ml. of the active compound, in the form of an intravenous infusion solution. For the preparation of aqueous isotonic solutions, the acids and salts of general Formula I are particularly suitable. To increase the solubility, alcohols, such as ethanol and propylene glycol, can be added. Furthermore advantageous are suppositories for intravaginal application, which can be readily manufactured.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The temperatures in the following examples are indicated in degrees Celsius.

EXAMPLE 1

(5Z,13E)-(8R,9S,11R,12R,15S)-9,11,15-Trihydroxy-19-methyl 5,13,18-prostatriemoic Acid and the Methyl Ester Thereof General Formula I: A=cis-CH=CH; B=trans-CH=CH;

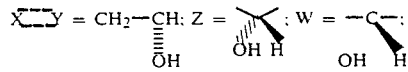

$R_1$ =COOH, COOCH$_3$; $R_2$, $R_3$ =H; $R_4$, $R_5$ =CH$_3$.

(a) 4-Bromo-2-methyl-2-butane (Dimethyl Allyl Bromide)

65.6 g. of freshly distilled isoprene was combined at −15° with 212 g. of a 36.7% hydrogen bromide solution in glacial acetic acid. The reaction mixture was stored for two days in a refrigerator (−6°), and then poured on 1.5 l. of ice water. The thus-isolated oil was separated, and the water phase was extracted three times with methylene chloride. The combined organic phases were dried over magnesium sulfate, concentrated on a rotary evaporator, and then fractionated under vacuum, thus obtaining 87 g. of the title compound, b.p. (30 mm.) 41°–50°.

(As a by-product, 2,4-dibromo-2-methylbutane was isolated, b.p. [5 mm.] 45°–48°.)

(b) 2-Carbethoxy-5-methyl-4-hexenoic Acid Ethyl Ester (Dimethylallylmalonic Acid Diethyl Ester)

A three-necked flask equipped with a reflux condenser, a dropping funnel, and an agitator was charged with 11.5 g. of sodium (cut into small pieces). Then, 250 ml. of absolute ethanol was added dropwise so quickly that the solution continued to boil vigorously. To the hot alcoholate solution were added dropwise 80 g. of freshly distilled diethyl malonate and then 78 g. of the dimethyl allyl bromide obtained in accordance with (a). After one hour of agitation under heating, the solution showed a neutral reaction. The thus-precipitated sodium bromide was filtered off, the precipitate was washed with ether and methylene chloride, and the filtrate was shaken with sodium chloride solution. The organic phase was dried over magnesium sulfate, concentrated on a forced circulation evaporator, and twice fractionated under vacuum, thus producing 99 g. of the desired compound, b.p. (13 mm.) 130°–132° and (6 mm.) 100°–106°, respectively.

(c) 2-Carboxy-5-methyl-4-hexenoic Acid (Dimethylallylmalonic Acid)

22.8 g. of the diester obtained in the preceding reaction stage was heated under reflux for 4 hours together with 19.6 g. of potassium hydroxide in 25 ml. of water and 50 ml. of ethanol. Thereafter, the ethanol was withdrawn with the aid of a forced circulation evaporator, the residue was dissolved in 25 ml. of water and combined under ice cooling dropwise with concentrated hydrochloric acid to pH 1. The aqueous phase was then extracted with ether five times. The combined ether extracts were washed with a small amount of saturated sodium chloride solution, dried over magnesium sulfate, and evaporated to dryness. The residue was recrystallized from benzene, thus obtaining 13.7 g. of final product, m.p. 96°–97°.

(d) 5-Methyl-4-hexenoic Acid (Dimethylallylacetic Acid)

15 g. of the dicarboxylic acid obtained according to (c) was heated in a distillation apparatus to 150°–160°; during this step, carbon dioxide escaped. The product was then distilled under vacuum, thus obtaining 10.1 g. of final product, b.p. (10 mm.) 102°–107°.

As a by-product, 5,5-dimethyl-δ-valerolactone was produced; this compound was separated completely by distillation during the subsequent reaction stage of esterifying the carboxylic acid with diazomethane.

(e) 5-Methyl-4-hexenoic Acid Methyl Ester (Dimethylallylacetic Acid Methyl Ester)

13.1 g. of the carboxylic acid obtained according to (d) was combined with such a quantity of ethereal diazomethane solution that there was no longer any evolution of nitrogen during the addition of the reagent and the yellow coloring of the reaction solution was preserved. The solvent was then removed under vacuum and the residue fractionated under vacuum, thus obtaining 10 g. of the desired compound, b.p. (13 mm.) 59°–69°.

(f) (6-Methyl-2-oxo-5-heptenylidene)-triphenylphosphorane 42.9 g. of triphenylmethylphosphonium bromide (dried for 4 hours at 40° with the aid of an oil pump) was suspended in 400 ml. of absolute ether and combined dropwise with 53 ml. of n-butyllithium solution in hexane. The reaction solution was stirred overnight at room temperature and under argon. Then, within one hour, 8.2 g. of the ester obtained according to (e), dissolved in 100 ml. of absolute ether, was added dropwise to the yellow ylene solution. After stirring for 1.5 hours at room temperature, the white precipitate was separated, dissolved in water, and extracted with ether. The ether extracts were combined with the filtrate, washed with saturated sodium chloride solution, dried over magnesium sulfate, concentrated, and purified by column chromatography on silica gel with hexane/5–0–100% ethyl acetate as the eluent, thus obtaining 12.34 g. of the title compound.

(g) (1S,5R,6R,7R)-7-Benzoyloxy-6-[(E)-7-methyl-3-oxo-1,6-octadienyl]-2-oxabicyclo[3,3,0]octan-3-one 3.9 g. of (1S,5R,6R,7R)-6-formyl-7-benzoyloxy-2-oxabicyclo[3,3,0]octan-3-one [E. J. Corey et al., J. Amer. Chem. Soc. 91:5675 (1969)] and 5.5 g. of the phosphorane produced according to (f) were dissolved in 110 ml. of absolute benzene and stirred under argon for 5.5 hours at room temperature. Subsequently the reaction solution was evaporated to dryness on a forced circulation evaporator, and the residue was purified by column chromatography on silica gel with hexane/2–0–40% ethyl acetate as the eluent, thus obtaining 3.8 g. of the title compound.

(h) (1S,5R,6R,7R,3'S)-7-Benzoyloxy-6-[(E)-3-hydroxy-7-methyl-1,6-octadienyl]-2-oxabicyclo[3,3,0]octan-3-one 1.9 g. of the ketone obtained in the preceding reaction stage was dissolved in 132 ml. of dimethoxyethane (distilled over lithium aluminum hydride), combined with 135 ml. of ethereal zinc borohydride solution, and stirred for 2.5 hours under argon at room temperature. The reaction solution was then diluted with 100 ml. of ether and thereafter combined dropwise with 10 ml. of water. The mixture was stirred for another 10 minutes, then decanted, and the precipitate was washed with ether. The combined ether phases were washed with water, dried over magnesium sulfate, and concentrated to dryness. In total, four such reactions were conducted. The combined residues were purified by being chromatographed twice over a column on silica gel with methylene chloride/1–4% ethanol as the eluent. As the first product, the desired 15 α-alcohol was eluted (2.4 g.).

(i) (2RS,3aR,4R,5R,6aS,3'S)-4-[(E)-3-Hydroxy-7-methyl-1,6-octadienyl]-5-hydroxyperhydrocyclopenta[b]furan-2-ol Under argon, 4.54 ml. of a 20% solution of diisobutylaluminum hydride in toluene was added dropwise at −65° to a solution of 400 mg. of the 15 α-alcohol lactone obtained according to (h) in 16.5 ml. of absolute toluene. The mixture was agitated for 30 minutes and then 1.65 ml. of isopropanol was added dropwise to the reaction solution. The temperature was then allowed to rise to 0°. The mixture was combined with 16.5 ml of water and agitated for 10 minutes. Then, the mixture was extracted three times with methylene chloride, the organic phases were combined, washed with saturated sodium chloride solution, dried over sodium sulfate, and concentrated to dryness, thus obtaining 353 mg. of lactol as a colorless oil; this product was utilized in the subsequent reaction stage without further purification.

(j) A solution of 2.82 g. of 4-carboxybutyltriphenylphosphonium bromide in 3 ml. of absolute dimethyl sulfoxide was combined with 12.2 ml. of a solution of sodium methanesulfinylmethylate in absolute dimethyl sulfoxide (solution: 2 g. 50% sodium hydride suspension in 40 ml. of absolute dimethyl sulfoxide was stirred for one-half hour at 70°), by adding the latter solution dropwise to the former. The mixture was agitated for 30 minutes at room temperature. This ylene solution was then added dropwise at 15° to a solution of 353 mg. of the lactol obtained according to (i) in 5 ml. of absolute dimethyl sulfoxide within 15 minutes and then stirred for 2.75 hours at 35°. Then, 40 ml. of ice water was added to the reaction solution and the latter was extracted three times with ether. The organic extract was discarded. The aqueous phase was adjusted to pH 4 with 10% citric acid solution and extracted in succession respectively three times with a mixture of hexane/ether=1/1 and methylene chloride. The organic phases were then washed with saturated sodium chloride solution, dried over sodium sulfate, and concentrated under vacuum. The evaporation residues were purified by chromatography on silica gel with ethyl acetate/methanol as the eluent, thus obtaining 210 mg. of the prostatrienoic acid set forth in the title.

(k) The prostatrienoic acid obtained according to (j) was dissolved in a small amount of methylene chloride and combined with ethereal diazomethane solution. The mixture was stirred for a brief period of time and then excess diazomethane and the solvent were removed under vacuum. The evaporation residue was purified by column chromatography on silica gel with methylene chloride/1–8% ethanol as the eluent, thus obtaining 180 mg. of the methyl ester of prostatrienoic acid set forth in the title.

IR: 3390, 3000–2860, 1735, 1670, 1650, 1440, 1170, 1055, 1020 cm$^{-1}$.

EXAMPLE 2

(5Z,13E)-(8R,9S,11R,12R,15R)-9,11,15-Trihydroxy-19-methyl-5,13,18-prostatrienoic Acid and the Methyl Ester Thereof General Formula I: A=cis-CH=CH; B=trans-CH=CH;

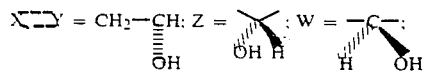

$R_1$=COOH, COOCH$_3$; $R_2$, $R_3$=H; $R_4$, $R_5$=CH$_3$.

In the reaction, described in Example 1(h), of (1S,5R,6R,7R)-7-benzoyloxy-6-[(E)-7-methyl-3-oxo-1,6-octadienyl]-2-oxabicyclo[3,3,0]octan-3-one with zinc borohydride solution, the 15β-alcohol was eluted as the second product from the column:

(a)
(1S,5R,6R,7R,3'R)-7-Benzoyloxy-6-[(E)-3-hydroxy-7-methyl-1,6-octadienyl]-2-oxabicyclo[3,3,0]octan-3-one The yield was 2.6 g. of the desired compound.

(b)
(2RS,3aR,4R,5R,6aS,3'R)-4-[(E)-3-Hydroxy-7-methyl-1,6-octadienyl]-5-hydroxyperhydrocyclopenta[b]furan-2-ol Under argon, 4.54 ml. of a 20% solution of diisobutyl aluminum hydride in toluene was added dropwise to a solution of the 15β-alcohol lactone obtained according to (a) in 16.5 ml. of absolute toluene, cooled to −65°. After 30 minutes, the reaction was terminated by the dropwise addition of 1.65 ml. of isopropanol and—after allowing the temperature to rise to 0°—of 16.5 ml. of water. Thereafter, the mixture was stirred for another 10 minutes and then extracted three times with methylene chloride; the organic phases were combined, washed with saturated sodium chloride solution, dried over sodium sulfate, and evaporated under vacuum. There remained 296 mg. of lactol as a colorless oil; this product was utilized in the subsequent reaction stage without further purification.

(c) The procedure indicated in Example 1(j) for the preparation of the 15α-alcohol was utilized in reacting the 296 mg. of lactol obtained according to (b) with the ylene produced from 2.82 g. of 4-carboxybutyltriphenylphosphonium bromide and 12.2 ml. of a solution of sodium methanesulfinylmethylate in absolute dimethyl sulfoxide to prepare the prostatrienoic acid set forth in the title. Here again, the evaporation residues of the extracts were purified by chromatography on silica gel (ethyl acetate/methanol), thus obtaining 150 mg. of the prostatrienoic acid set forth in the title.

(d) The prostatrienoic acid produced according to (c) was reacted with ethereal diazomethane solution according to the directions set forth in Example 1(k). After purification by chromatography on silica gel with methylene chloride/1–6% ethanol as the eluent, 110 mg. of the methyl ester of prostatrienoic acid indicated in the title was obtained.

IR: 3400, 3000–2860, 1737, 1670, 1650, 1440, 1170, 1055, 1025 cm$^{-1}$.

EXAMPLE 3

(5Z,13E)-(8R,11R,12R,15S)-9-Oxo-11,15-dihydroxy-19-methyl-5,13,18-prostatrienoic Acid and the Methyl Ester Thereof General Formula I: A=cis-CH=CH; B=trans-CH=CH;

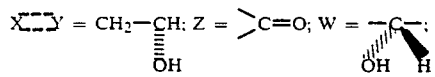

$R_1$=COOH, COOCH$_3$; $R_2$, $R_3$=H; $R_4$, $R_5$=CH$_3$.

(a)
(1S,5R,6R,7R,3'RS)-6-[(E)-3-Hydroxy-7-methyl-1,6-octadienyl]-7-hydroxy-2-oxabicyclo[3,3,0]octan-3-one A solution of 3.85 g. of (1S,5R,6R,7R,3'RS)-6-[(E)-7-methyl-3-hydroxyoctane-1,6-dienyl]-7-benzoyloxy-2-oxabicyclo[3,3,0]octan-3-one [a mixture of the 15α- and 15β-alcohols 1(h) and 2(a) obtained in accordance with the description of Example 1(h)] dissolved in 200 ml. of absolute methanol, was combined with 1.4 g. of potassium carbonate (anhydrous), and stirred for two hours at room temperature and under argon. Thereafter, 202 ml. of 0.1N hydrochloric acid was added to the reaction mixture and the latter was stirred for another 15 minutes. After concentration of the solution, the latter was extracted with ethyl acetate, the combined organic phases were then washed with saturated sodium chloride solution, dried, and evaporated to dryness. The residue was purified by column chromatography on silica gel with methylene chloride/2-10% isopropanol, thus obtaining 2.2 g. of the title compound.

(b)
(1S,5R,6R,7R,3'S)-6-[(E)-7-Methylocta-1,6-dienyl]-3',7-bis(tetrahydropyran-2-yloxy)-2-oxabicyclo[3,3,-0]octan-3-one At ice bath temperature, 8.6 ml. of 2,3-dihydropyran (freshly distilled over potassium hydroxide) and 19 mg. of p-toluenesulfonic acid were added to a solution of 2.2 g. of the diol obtained according to (a) in 70 ml. of methylene chloride. The mixture was agitated for 15 minutes at 0°, then diluted with methylene chloride, and extracted with sodium bicarbonate solution. The organic phase was washed with water, dried over magnesium sulfate, and evaporated to dryness. A preliminary purification by column chromatography on silica gel with ether as the eluent yielded 4.5 g. of the bis(tetrahydropyranyl) ether.

(c)
(2RS,3aR,4R,5R,6aS,3'RS)-4-[(E)-7-Methylocta-1,6-dienyl]-3',5-bis(tetrahydropyran-2-yloxy)perhydrocyclopenta[b]furan-2-ol Under argon, 39.2 ml. of a 20% diisobutyl aluminum hydride solution in toluene was added dropwise to a solution of 4.5 g. of lactone obtained in the preceding reaction stage in 150 ml. of absolute toluene, cooled to −65°. The mixture was agitated for 30 minutes, then 3.6 ml. of isopropanol was added dropwise thereto, and at 0° 25 ml of water was furthermore introduced. The mixture was stirred for another 10 minutes. The thus-produced white precipitate was removed by way of a porous filter plate and washed with methylene chloride. The organic phases were washed with saturated sodium chloride solution, dried over sodium sulfate, and evaporated to dryness. Yield: 4.4 g. of an oil which was used without further purification in the next reaction stage.

(d)
(5Z,13E)-(8R,9S,11R,12R,15RS)-9-Hydroxy-19-methyl-11,15-bis(tetrahydropyran-2-yloxy)-5,13,18-prostatrienoic Acid 75.3 ml. of a solution of sodium methanesulfinyl-methylate in absolute dimethyl sulfoxide (solution: 5 g. of 50% sodium hydride suspension was stirred in 100 ml. of absolute dimethyl sulfoxide for one-half hour at 70°) was added dropwise to a solution of 17.3 g. of 4-carboxybutyltriphenylphosphonium bromide in 73 ml. of absolute dimethyl sulfoxide. After 30 minutes of agitation at room temperature, this ylene solution was added dropwise at 15° within 15 minutes to a solution of the 4.4 g. of lactol obtained in the preceding reaction step in 73 ml. of absolute dimethyl sulfoxide. The reaction mixture was then agitated for 2 hours at 35°. The mixture was then combined with 145 ml. of water and extracted three times with ether. The organic extract was discarded. The aqueous phase was adjusted to pH 4 with 10% citric acid solution and extracted respectively three times with a mixture of ether/hexane=1/1 and methylene chloride. As determined by TLC, the methylene chloride phase could be discarded. The ether/hexane extract was washed with saturated sodium chloride solution, dried, and concentrated on a forced circulation evaporator, thus obtaining 2.6 g. of the desired compound.

(e)
(5Z,13E)-(8R,11R,12R,15RS)-19-Methyl-9-oxo-11,15-bis(tetrahydropyran-2-yloxy)-5,13,18-prostatrienoic Acid At −20°, a solution of 2.6 g. of the alcohol obtained according to (d) in 33 ml. of acetone was combined with 2.72 ml. of Jones reagent and stirred for 30 minutes at this temperature. Thereafter, 3.3 ml. of isopropanol was added dropwise thereto, the mixture was stirred for another 10 minutes at −20°, diluted with ether, and washed three times with water. The organic phase was dried over magnesium sulfate and concentrated under vacuum, thus obtaining 2 g. of the title compound.

(f) 2 g. of the bis(pyranyl) ether obtained in the preceding reaction stage was stirred for 3.5 hours at 30° in 44 ml. of a mixture consisting of 65 parts of glacial acetic acid, 35 parts of water, and 10 parts of tetrahydrofuran. The mixture was then concentrated several times at room temperature with benzene under an oil pump vacuum. There remained 1.7 g. of product. By chromatography on silica gel (ethyl acetate/methanol), it was possible to separate the prostatrienoic acid indicated in the title as the more polar product.

(g) Analogously to the directions given in Example 1(k), the prostatrienoic acid methyl ester of the title was produced by esterification of the acid obtained in the preceding reaction stage with diazomethane; an even more advantageous procedure was followed by esterification of the 15α,β-OH-acid mixture and subsequent chromatographic separation of the more polar, desired 15α-alcohol methyl ester with methylene chloride/-1-4% ethanol as the eluent.

IR: 3400, 3000-2860, 1740, 1670, 1650, 1440, 1160, 1075 cm$^{-1}$.

EXAMPLE 4

(5Z,13E)-(8R,11R,12R,15R)-9-Oxo-11,15-dihydroxy-19-methyl-5,13,18-prostatrienoic acid and the Methyl Ester Thereof General Formula I: A=cis-CH=CH; B=trans-CH=CH;

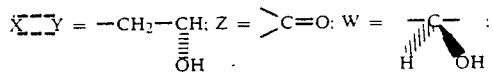

$R_1$=COOH, COOCH$_3$; $R_2$, $R_3$=H; $R_4$, $R_5$=CH$_3$.

(a) The prostatrienoic acid mentioned in the title was obtained by chromatographic separation as the less polar product from the product mixture produced in Example 3(f).

(b) The methyl ester of prostatrienoic acid indicated in the title was obtained either analogously to the esterification with diazomethane described in Example 1(k) from the prostatrienoic acid set forth in the title and indicated under (a) or, more advantageously, by chromatographic separation as the less polar product from the 15-isomer mixture produced by diazomethane esterification (of the 15α,β-OH-acid mixture obtained according to the directions in Example 3[f]), using methylene chloride/1–4% ethanol as the eluent.

EXAMPLE 5

(5Z,10Z,13E)-(8R,12R,15S)-15-Hydroxy-9-oxo-19-methyl-5,10,13,18-prostatetraenoic Acid and the Methyl Ester Thereof General Formula I: A=cis-CH=CH; B=trans-CH=CH;

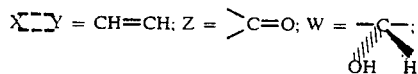

$R_1$=COOH, COOCH$_3$; $R_2$, $R_3$=H; $R_4$, $R_5$=CH$_3$.

A solution of 77 mg. of (5Z,13E)-(8R,11R,12R,15S)-9-oxo-11,15-dihydroxy-19-methyl-5,13,18-prostatrienoic acid (from Example 3) in 6 ml. of 90% acetic acid was stirred for 19 hours at 60° and then evaporated under vacuum. After chromatography on silica gel (ether/5% dioxane), the prostatetraenoic acid was esterified with ethereal diazomethane solution, thus obtaining 40 mg. of the title compound as a slightly yellowish oil.

IR: 3400, 3000–2860, 1730, 1700, 1670, 1650, 1590, 1440, 1170, 1040 cm$^{-1}$.

EXAMPLE 6

(5Z,10Z,13E)-(8R,12R,15R)-15-Hydroxy-9-oxo-19-methyl-5,10,13,18-prostatetraenoic Acid and the Methyl Ester Thereof General Formula I: A=cis-CH=CH; B=trans-CH=CH;

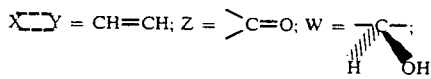

$R_1$=COOH, COOCH$_3$; $R_2$, $R_3$=H; $R_4$, $R_5$=CH$_3$.

In accordance with the directions given in Example 5, the title compounds were produced from the compound described in Example 4.

IR: 3400, 3000–2860, 1730, 1705, 1675, 1650, 1590, 1440, 1165, 1045 cm$^{-1}$.

EXAMPLE 7

(5Z,13E)-(8R,11R,12R,15S)-15-Hydroxy-9-oxo-11,19-dimethyl-5,13,18-prostatrienoic Acid and the Methyl Ester Thereof General Formula I: A=cis-CH=CH; B=trans-CH=CH;

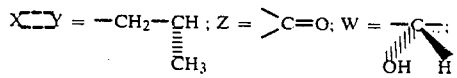

$R_1$=COOH, COOCH$_3$; $R_2$, $R_3$=H; $R_4$, $R_5$=CH$_3$.

590 mg. of copper(I) iodide was suspended under argon in 30 ml. of absolute ether and then combined under agitation at 0° dropwise with 4 ml. of 2-molar methyllithium solution in ether within 20 minutes. After stirring for another 15 minutes, the mixture was cooled to −40° and then combined dropwise with 240 mg. of (5Z,10Z,13E)-(8R,12R,15S)-15-hydroxy-9-oxo-19-methyl-5,10,13,18-prostatetraenoic acid (from Example 5). The reaction solution was allowed to warm up within 45 minutes to −10° and was then further stirred at 0° for 45 minutes. Thereafter, the mixture was gently combined with small ice cubes and with about 100 ml. of saturated ammonium chloride solution. The mixture was thereafter extracted with ether, the combined organic phases were shaken with saturated sodium chloride solution, dried over magnesium sulfate, and concentrated under vacuum. The prostatrienoic acid was then esterified with ethereal diazomethane solution. After chromatography on silica gel (ether/pentane), 160 mg. of the title compound was obtained.

IR: 3400, 3000–2860, 1740, 1670, 1650, 1440, 1160, 1055 cm$^{-1}$.

EXAMPLE 8

(5Z,13E)-(8R,11R,12R,15R)-15-Hydroxy-9-oxo-11,19-dimethyl-5,13,18-prostatrienoic Acid and the Methyl Ester Thereof General Formula I: A=cis-CH=CH; B=trans-CH=CH;

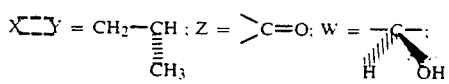

$R_1$=COOH, COOCH$_3$; $R_2$, $R_3$=H; $R_4$, $R_5$=CH$_3$.

The title compounds were prepared from the compound described in Example 5 in accordance with the directions given in Example 7.

IR: 3400, 3000–2850, 1740, 1670, 1650, 1440, 1165, 1050 cm$^{-1}$.

EXAMPLE 9

(5Z,13E)-(8R,11R,12R,15S)-11-Cyano-15-hydroxy-9-oxo-19-methyl-5,13,18-prostatrienoic Acid and the Methyl Ester Thereof General Formula I: A=cis-CH=CH; B=trans-CH=CH;

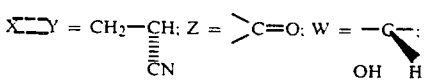

$R_1$=COOH, COOCH$_3$ $R_2$, $R_3$=H; $R_4$, $R_5$=CH$_3$.

A solution of 400 mg. of (5Z,10Z,13E)-(8R,12R,15S)-15-hydroxy-9-oxo-19-methyl-5,10,13,18-prostatetraenoic acid (from Example 5) in a mixture of 1 ml. of acetone cyanohydrin and 5 ml. of methanol is combined with 1 ml. of 1% aqueous sodium carbonate. After refluxing for 16 hours, the cooled-off solution is introduced into water and extracted with ether. The combined ether extracts are washed with saturated sodium chloride solution, dried over magnesium sulfate, and concentrated under vacuum. Esterification with ethereal diazomethane solution and chromatography on silica gel (ether/pentane) yielded 290 mg. of the prostatrienoic methyl ester.

IR: 3400, 3000–2860, 2220, 1740, 1670, 1650, 1440, 1160, 1050 cm$^{-1}$.

EXAMPLE 10

(5Z,13E)-(8R,11R,12R,15R)-11-Cyano-15-hydroxy-9-oxo-19-methyl-5,13,18-prostatrienoic Acid and the Methyl Ester Thereof General Formula I: A=cis-CH=CH; B=trans-CH=CH;

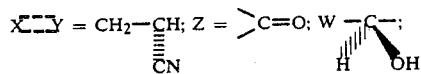

$R_1$=COOH, COOCH$_3$; $R_2$, $R_3$=H; $R_4$, $R_5$=CH$_3$.

In accordance with the directions given in Example 9, the title compounds were produced from the compound set forth in Example 6.

IR: 3400, 3000–2850, 2220, 1740, 1670, 1650, 1440, 1160, 1045 cm$^{-1}$.

EXAMPLE 11

(5Z,13E)-(8R,12R,15S)-15-Hydroxy-9-oxo-19-methyl-5,13,18-prostatrienoic Acid and the Methyl Ester Thereof General Formula I: A=cis-CH=CH; B=trans-CH=CH;

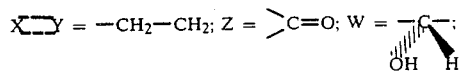

$R_1$=COOH, COOCH$_3$; $R_2$, $R_3$=H; $R_4$, $R_5$=CH$_3$.

The following compound served as the starting material:

(a) (5Z,10Z,13E)-(8R,12R,15S)-15-Acetoxy-9-oxo-19-methyl-5,10,13,18-prostatetraenoic Acid General formula I: A=cis-CH=CH; B=trans-CH=CH;

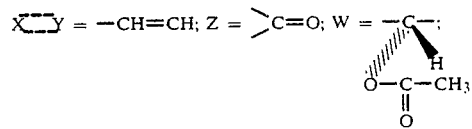

$R_1$=COOH; $R_2$, $R_3$=H; $R_4$, $R_5$=CH$_3$.

500 mg. of (5Z,10Z,13E)-(8R,12R,15S)-15-hydroxy-9-oxo-19-methyl-5,10,13,18-prostatetraenoic acid (from Example 5) was stirred for 24 hours in a mixture of 6 ml. of pyridine and 1.5 ml. of acetic anhydride at room temperature. The reaction mixture was then concentrated repeatedly with benzene on a forced circulation evaporator; the residue was taken up in ether and washed with saturated sodium chloride solution. The ether phase was dried over magnesium sulfate and concentrated to dryness under vacuum. The residue (490 mg.) was utilized in the subsequent reaction stage without further purification.

(b) (5Z,13E)-(8R,9RS,12R,15S)-15-Acetoxy-9-hydroxy-19-methyl-5,13,18-prostatrienoic Acid General Formula I: A=cis-CH=CH; B=trans-CH=CH;

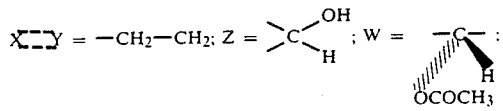

$R_1$=COOH; $R_2$, $R_3$=H; $R_4$, $R_5$=CH$_3$.

The 490 mg. of product obtained according to (a) was dissolved in 10 ml. of methanol, cooled to −20°, and combined dropwise with a solution of 0.7 g. of sodium borohydride in 9 ml. of methanol and 1 ml. of water, likewise cooled to −20°. After stirring for 15 minutes under argon, a solution of 0.7 ml. of glacial acetic acid in 10 ml. of water was added to the reaction mixture. The mthanol was removed under vacuum at room temperature. Subsequently, the aqueous phase was extracted repeatedly with methylene chloride. The combined organic phases were washed neutral and concentrated on a forced circulation evaporator, thus obtaining 480 mg. of oily substance which was used in the next reaction stage without further purification.

(c) (5Z,13E)-(8R,12R,15S)-15-Acetoxy-9-oxo-19-methyl-5,13,18-prostatrienoic Acid General Formula I: A=cis-CH=CH; B=trans-CH=CH;

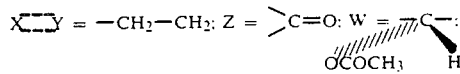

$R_1$=COOH; $R_2$, $R_3$=H; $R_4$, $R_5$=CH$_3$.

The 480 mg. of reaction product obtained in the preceding reaction stage was dissolved in 12 ml. of acetone, cooled to −30°, and combined with 0.5 ml. of Jones reagent. After 30 minutes of agitation under an argon atmosphere, the reaction was terminated by the dropwise addition of 0.5 ml. of isopropanol. The mixture was further stirred for 5 minutes, diluted with methylene chloride, and washed with saturated sodium chloride solution. The organic phase was dried over magnesium sulfate and concentrated to dryness, thus obtaining 450 mg. of product which was utilized without further purification in the subsequent reaction stage.

(d) The 450 mg. of product obtained in the preceding reaction stage was stirred together with 350 mg. of anhydrous potassium carbonate in 50 ml. of methanol for 80 minutes at room temperature under an argon atmosphere. The methanol was then withdrawn with the use of a forced circulation evaporator, the residue was combined with water and extracted repeatedly with methylene chloride. The combined organic phases were washed with saturated sodium chloride solution, dried over magnesium sulfate, and concentrated under vacuum. The thus-obtained prostatrienoic acid mentioned in the title was converted into the corresponding methyl ester by reaction with ethereal diazomethane solution. After purification by chromatography on silica gel (ether/pentane), 300 mg. of final product was obtained as a colorless oil.

IR: 3400, 3000–2860, 1740, 1670, 1650, 1440, 1160, 1045 cm$^{-1}$.

EXAMPLE 12

(5Z,13E)-(8R,12R,15R)-15-Hydroxy-9-oxo-19-methyl-5,13,18-prostatrienoic Acid and the Methyl Ester Thereof General Formula I: A=cis CH=CH; B=trans-CH=CH;

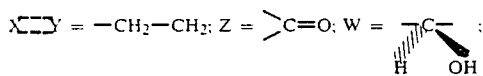

$R_1$=COOH, COOCH$_3$; $R_2$, $R_3$=H; $R_4$, $R_5$=CH$_3$.

The title compound was obtained, starting with (5Z,10Z,13E)-(8R,12R,15R)-15-hydroxy-9-oxo-19-methyl-5,10,13,18-prostatetraenoic acid (from Example 6) analogously to the reaction sequence described in Example 11.

IR: 3400, 3000–2860, 1740, 1670, 1650, 1440, 1160, 1045 cm$^{-1}$.

EXAMPLE 13

(13E)-(8R,9S,11R,12R,15S)-9,11,15-Trihydroxy-19-methyl-13,18-prostadienoic Acid and the Methyl Ester Thereof General Formula I: A=—CH$_2$—CH$_2$; B=trans-CH=CH;

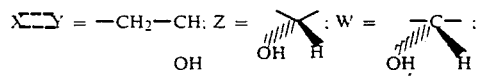

$R_1$=COOH, COOCH$_3$; $R_2$, $R_3$=H; $R_4$, $R_5$=CH$_3$.

The following compound served as the starting material:

(a)
(1S,5R,6R,7R)-6-Diethoxymethyl-7-benzoyloxy-2-oxabicyclo[3,3,0]octan-3-one 7.7 g. of (1S,5R,6R,7R)-6-formyl-7-benzoyloxy-2-oxabicyclo[3,3,0]octan-3-one was dissolved in 80 ml. of absolute dimethoxyethane, combined with 13.29 g. of ethyl orthoformate in 30 ml. of absolute ethanol and 120 mg. of p-toluenesulfonic acid and stirred overnight at room temperature under argon. Thereafter, the reaction mixture was diluted with ether and shaken in succession three times with 100 ml. of sodium bicarbonate solution as well as 100 ml. of water. The organic phase was dried over sodium sulfate and concentrated to dryness, thus obtaining 8.55 g. of the desired compound.

(b)
(1S,3RS,5R,6R,7R)-3,7-Dihydroxy-6-diethoxymethyl-2-oxabicyclo[3,3,0]octan-3-one Under argon, 87.3 ml. of a 20% solution of diisobutyl aluminum hydride in toluene was added dropwise to a solution of 8.55 g. of the lactone acetal obtained in the preceding reaction stage in 370 ml. of absolute toluene at −70°. After 30 minutes, the reaction was terminated by the dropwise addition of 8.4 ml. of isopropanol and 46 ml. of water. While the reaction solution warmed up to room temperature, the agitation was continued (for about 30 minutes). Thereafter, the mixture was combined with 275 ml. of methylene chloride, stirred for another 15 minutes, filtered, the aqueous phase separated, and the organic phase dried over magnesium sulfate. After concentration of the reaction solution at room temperature, the residue (together with the residue of a parallel batch of equal size) was utilized in the subsequent reaction stage without further purification.

(c)
(5Z)-(8R,9S,11R,12R)-9,11-Dihydroxy-13,13-diethoxy-14,15,16,17,18,19,20-heptanor-5-prostenoic Acid At 18°–20°, 236 ml. of a solution of sodium methanesulfinylmethylate in absolute DMSO (prepared by one hour of heating of 15 g. 50% sodium hydride suspension in 300 ml. of absolute DMSO to 70°) was added dropwise to a solution of 57 g. of 4-carboxybutyltriphenylphosphonium bromide in 175 ml. of absolute dimethyl sulfoxide. The solution, which had a reddish-brown color, was stirred for 30 minutes at room temperature. This ylene solution was thereafter added dropwise under water cooling to a solution of the evaporation residue of the 8.55 g. of product described in Example (b) in 52 ml. of abolute DMSO, and then stirred for 2 hours at 50° under argon. After cooling, the mixture was combined with ice water, stirred for another 15 minutes, and then extracted three times with ether. The extract was discarded. The aqueous phase was adjusted to pH 4 with 10% citric acid solution and extracted in sucession with a mixture of ether/hexane 2:1 and methylene chloride. The organic phases were dried over sodium sulfate and concentrated at 30° on an oil pump. The evaporation residue of the methylene chloride extract became solid and was extracted with ethyl acetate. While the substance insoluble in ethyl acetate could be discarded, the ethyl acetate and ether/hexane evaporation residues were purified by chromatography on silica gel (hexane/ethyl acetate/methanol), thus obtaining 4.8 g. of the desired compound.

(d)
(5Z)-(8R,9S,11R,12R)-9,11-Diacetoxy-13,13-diethoxy-14,15,16,17,18,19,20-heptanor-5-prostenoic Acid A solution of 4.8 g. of the compound obtained in the preceding reaction stage in 30 ml. of pyridine was added dropwise under ice cooling to a mixture of 20 ml. of pyridine and 10 ml. of acetic anhydride and stirred for 20 hours at room temperature. The mixture was then repeatedly concentrated with benzene under vacuum and the residue taken up in ether and washed neutral with saturated sodium chloride solution. The organic phase was dried over magnesium sulfate and concentrated to dryness under vacuum (optionally by the repeated addition of benzene), thus obtaining 5.7 g. of the desired compound.

(e)
(8R,9S,11R,12R)-9,11-Diacetoxy-13,13-diethoxy-14,15,16,17,18,19,20-heptanor-prostanoic Acid The 5.7 g. of compound obtained according to the directions in Example 13(d) was mixed with 500 mg. of 10% palladium on charcoal and stirred with 250 ml. of ethyl acetate for 2 hours at −20° under a hydrogen atmosphere. After filtration, the product was evaporated to dryness under vacuum, thus producing 5.6 g. of the title compound as a colorless oil.

(f)
(8R,9S,11R,12R)-9,11-Diacetoxy-13-oxo-14,15,16,17,18,19,20-heptanor-prostanoic Acid The 5.6 g. of diethoxy acetal obtained in the preceding reaction stage was stirred in 80 ml. of a solution of glacial acetic acid/water/tetrahydrofuran (65:35:10) for 40 hours at room temperature. Then, the mixture was evaporated several times under vacuum while adding benzene, thus obtaining 4 g. of the title compound which was used without further purification in the subsequent reaction stage.

(g) (13E)-(8R,9S,11R)-9,11-Diacetoxy-15-oxo-19-methyl-13,18-prostadienoic Acid

A solution of 2 g. of the diacetoxy aldehyde obtained in the preceding stage and 2.3 g. of the ylene prepared according to Example 1(f) in 200 ml. of benzene was stirred together with 0.5 g. of benzoic acid at 40° until the control of the reaction by thin-layer chromatography indicated that the reaction was complete. Thereafter, the solvent was withdrawn under vacuum, the residue was taken up in ether, the organic phase was washed with saturated sodium chloride solution, dried over magnesium sulfate, and then concentrated to dryness on a forced circulation evaporator. The residue of the evaporation was purified by chromatography on silica gel (hexane/ethyl acetate/methanol), thus obtaining 1.3 g. of the desired compound.

(h) (13E)-(8R,9S,11R,15S)-9,11-Diacetoxy-15-hydroxy-19-methyl-13,18prostadienoic Acid and (13E)-(8R,9S,11R,15R)-9,11-Diacetoxy-15-hydroxy-19-methyl-13,18-prostadienoic Acid A solution of the 1.3 g. of ketone produced in the preceding reaction stage in 80 ml. of dimethoxyethane, freshly distilled over lithium aluminum hydride, was combined in an argon atmosphere with 80 ml. of ethereal zinc borohydride solution and stirred for 70 minutes at room temperature. Subsequently, the reaction solution, diluted with ether, was carefully combined with 10 ml. of water and stirred for another 10 minutes. The organic phase was washed with saturated sodium chloride solution, dried over magnesium sulfate, and concentrated under vacuum. The residue (1 g.) was utilized in the subsequent reaction stage.

(i) The one gram of 15α,β-alcohol mixture obtained in the preceding reaction stage was agitated together with 700 mg. of anhydrous potassium carbonate in 80 ml. of methanol for 50 minutes at room temperature in an argon atmosphere. After removal of the solvent under vacuum, the residue was combined with sodium chloride solution and extracted with ether. The organic phase was dried over magnesium sulfate, concentrated, and then, either by chromatography on silica gel (ethyl acetate/methanol) the prostadienoic acid of the title was separated as the more polar product; or (j) by reaction with ethereal diazomethane solution the mixture was reacted to the prostadienoic methyl ester mentioned in the title, which can be separated as the more polar product (170 mg.) by chromatography on silica gel (methylene chloride/1-8% ethanol).

IR: 3400, 3000-2860, 1735, 1670, 1650, 1440, 1170, 1055, 1020 cm$^{-1}$.

EXAMPLE 14

(13E)-(8R,9S,11R,12R,15R)-9,11,15-Trihydroxy-19-methyl-13,18-prostadienoic Acid and the Methyl Ester Thereof General Formula I: A=—CH$_2$—CH$_2$; B=trans-CH=CH;

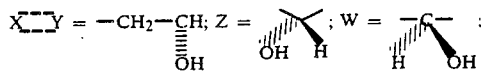

R$_1$=COOH, COOCH$_3$; R$_2$, R$_3$=H; R$_4$, R$_5$=CH$_3$.

The title compounds were separated, as the less polar products, from the reaction mixtures described in Example 13(i) and 13(j), respectively, by chromatography on silica gel.

IR: 3400, 3000-2900, 1735, 1670, 1650, 1440, 1170, 1055, 1020 cm$^{-1}$.

EXAMPLE 15

(13E)-(8R,11R,12R,15S)-9-Oxo-11,15-dihydroxy-19-methyl-13,18-prostadienoic Acid Methyl Ester General Formula I: A=—CH$_2$—CH$_2$; B=trans-CH=CH;

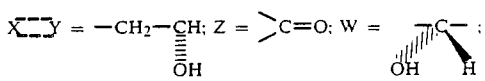

R$_1$=COOCH$_3$; R$_2$, R$_3$=H; R$_4$, R$_5$=CH$_3$.

At −45°, 1.2 ml. of N,N-diethyltrimethylsilylamine was added to a solution of 95 mg. of the triol obtained according to Example 13(j) in 4 ml. of absolute acetone; the mixture was agitated for 6.5 hours at −40°. Thereafter, the mixture was diluted with 30 ml. of ether previously cooled to −70°, shaken once with 5 ml. of ice-cooled sodium bicarbonate solution and twice with respectively 5 ml. of saturated sodium chloride solution, dried with sodium sulfate, and evaporated under vacuum. The 11,15-bis(trimethylsilyl ether) obtained in this way was dissolved in 16 ml. of absolute methylene chloride and combined at +5° with a solution of 665 mg. of Collins reagent (preparation see Org. Syntheses 52 :5). The mixture was stirred for 10 minutes, diluted with 50 ml. of ether, filtered, and evaporated under vacuum. To split off the silyl ether blocking groups, the residue was agitated with a mixture of 9 ml. of methanol. 0.9 ml. of water, and 0.45 ml. of glacial acetic acid for 45 minutes at room temperature. Thereafter, the mixture was diluted with 60 ml. of ether, shaken with 10 ml. of sodium bicarbonate solution and then shaken twice with respectively 10 ml. of saturated sodium chloride solution, dried over magnesium sulfate, and evaporated under vacuum. After purification by preparative layer chromatography (ether/dioxane 9+1 as the eluent) on silica gel plates, 60 mg. of the title compound was obtained as a colorless oil.

IR: 3400, 3000-2860, 1737, 1670, 1650, 1440, 1160, 1070 cm$^{-1}$.

EXAMPLE 16

(13E)-(8R,11R,12R,15R)-9-Oxo-11,15-dihydroxy-19-methyl-13,18-prostadienoic Acid Methyl Ester General Formula I: A=—CH$_2$—CH$_2$; B=trans-CH=CH;

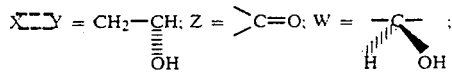

R$_1$=COOCH$_3$; R$_2$, R$_3$=H; R$_4$, R$_5$=CH$_3$.

Analogously to the directions set forth in Example 15, the title compound was obtained from the triol prepared in Example 14.

IR: 3400, 3000–2850, 1735, 1670, 1650, 1440, 1160, 1075 cm$^{-1}$.

EXAMPLE 17

(8R,9S,11R,12R,15S)-9,11,15-Trihydroxy-19-methyl-18-prostenoic Acid and the Methyl Ester Thereof General Formula I: A, B=—CH$_2$—CH$_2$;

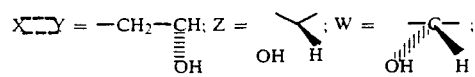

R$_1$=COOH, COOCH$_3$; R$_2$, R$_3$=H; R$_4$, R$_5$=CH$_3$.

The acid obtained according to 13(g) was reacted, after splitting off the blocking groups (analogously to 13[i]) and optionally after subsequent esterification, with sodium borohydride in analogy to Example 11(b), thus obtaining 190 mg. and 230 mg. of the title compounds, respectively, from 368 mg. of acid and 382 mg. of methyl ester, respectively, after separation by chromatography on silica gel (ethyl acetate/methanol or methylene chloride/1–5% ethanol).

IR: 3600–3400, 3000–2850, 1735, 1660, 1440, 1170, 1055 cm$^{-1}$.

EXAMPLE 18

(8R,9S,11R,12R,15R)-9,11,15-Trihydroxy-19-methyl-18-prostenoic Acid and the Methyl Ester Thereof General Formula I: A, B=—CH$_2$—CH$_2$;

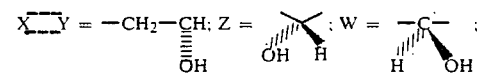

R$_1$=COOH, COOCH$_3$; R$_2$, R$_3$=H; R$_4$, R$_5$=CH$_3$.

Analogously to the directions in Example 17 for the 15α-isomer, the title compounds were obtained, starting with the compounds of Example 14.

IR: 3600–3400, 3000–2850, 1735, 1655, 1440, 1170, 1050 cm$^{-1}$.

EXAMPLE 19

(8R,11R,12R,15S)-9-Oxo-11,15-dihydroxy-19-methyl-18-prostenoic Acid and the Methyl Ester Thereof General Formula I: A, B=—CH$_2$—CH$_2$;

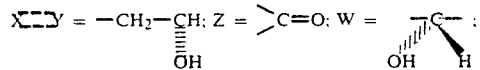

R$_1$=COOH, COOCH$_3$; R$_2$, R$_3$=H; R$_4$, R$_5$=CH$_3$.

The title compounds were prepared analogously to the directions in Example 15, starting with the trihydroxyprostenoic acid and/or its methyl ester obtained according to Example 17.

IR: 3400, 3000–2860, 1740, 1660, 1440, 1170, 1050 cm$^{-1}$.

EXAMPLE 20

(8R,11R,12R,15R)-9-Oxo-11,15-dihydroxy-19-methyl-18-prostenoic Acid and the Methyl Ester Thereof General Formula I: A, B=—CH$_2$—CH$_2$;

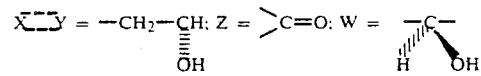

R$_1$=COOH, COOCH$_3$; R$_2$, R$_3$=H; R$_4$, R$_5$=CH$_3$.

Starting with the compounds prepared in accordance with Example 18, the title compounds were obtained analogously to the directions given in Example 17.

IR: 3400, 3000–2850, 1740, 1660, 1440, 1170, 1055 cm$^{-1}$.

EXAMPLE 21

(5Z,13E)-(8R,11R,12R,15S)-9-Oxo-11,15-dihydroxy-19-methyl-5,13,18-prostatrienoic Acid and the Methylsulfamide Thereof General Formula I: A=cis-CH=CH; B=trans-CH=CH;

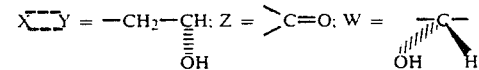

R$_1$=—CO—NH—SO$_2$CH$_3$; R$_2$, R$_3$=H; R$_4$, R$_5$=CH$_3$.

The 3′S-(tetrahydropyran-2-yloxy) compound of the isomeric mixture of Example 3(c), prepared from 1(h) [via the stages according to the directions in Examples 3(a), 3(b), and 3(c)], served as the educt.

(a)

(5Z,13E)-(8R,9S,11R,12R,15S)-9-Hydroxy-19-methyl-11,15-bis(tetrahydropyran-2-yloxy)-5,13,18-prostatrienoic Acid Methylsulfamide 2.09 g. of the above-mentioned educt was reacted with 46 ml. of a solution of sodium methanesulfinylmethylate in absolute dimethyl sulfoxide and 11.94 g. of 4-(carboxylic acid methylsulfamide)-butyltriphenylphosphonium bromide according to the directions set forth in Example 3(d). After chromatography on silica gel with ether/dioxane as the eluent, 1.5 g. of the title compound was obtained.

(b)

(5Z,13E)-(8R,11R,12R,15S)-19-Methyl-9-oxo-11,15-bis(tetrahydropyran-2-yloxy)-5,13,18-prostatrienoic Acid Methylsulfamide Analogously to the directions given in Example 3(e) 1.2 g. of the title compound was produced from the 1.5 g. of product obtained in the preceding reaction stage, by means of Jones oxidation.

(c) The 11- and 15-blocking groups were split off analogously to the directions in Example 3(f). From the 1.2 g. of product in the preceding reaction stage, 0.5 g of the title compound of Example 21 was obtained.

IR: 3400, 3000–2860, 1735, 1720, 1670, 1650, 1440, 1340, 1160, 1075 cm$^{-1}$.

EXAMPLE 22

(5Z,13E)-(8R,11R,12R,15R)-9-Oxo-11,15-dihydroxy-19-methyl-5,13,18-prostatrienoic Acid Methylsulfamide General Formula I: A=cis-CH=CH; B=trans-CH=CH;

$X\text{---}Y = -CH_2-\underline{CH}; Z = {>}C=O; W = \phantom{x}\overline{\phantom{x}}C\text{---}; $
$\phantom{xxxxxxxxxxxxxxxxx}\overline{\overline{OH}}\phantom{xxxxxxxxxxx}H\phantom{xx}\overline{O}H$ $R_1 = -CO-NH-SO_2CH_3$; $R_2$, $R_3 = H$; $R_4$, $R_5 = CH_3$.

Analogously to the reaction sequence described for Example 21, the title compound was obtained, starting with 2(a).

IR: 3400, 3000–2850, 1740, 1720, 1670, 1650, 1440, 1345, 1160, 1080 cm$^{-1}$.

EXAMPLE 23

(5Z,13E)-(8R,9S,11R,12R,15S)-1-Acetoxy-19-methyl-5,13,18-prostatriene-9,11,15-triol General Formula I: A=cis-CH=CH; B=trans-CH=CH;

$X\text{---}Y = -CH_2-\underline{CH}; Z = \phantom{x}\overline{\phantom{x}}\phantom{xx}; W = \phantom{x}\overline{\phantom{x}}C\text{---};$
$\phantom{xxxxxxxxxxxxxxxxx}\overline{\overline{OH}}\phantom{xx}\overline{O}H\phantom{xx}H\phantom{xxx}\overline{O}H\phantom{xx}H$ $R_1 = -CH_2O-\underset{\underset{O}{\|}}{C}-CH_3;$ $R_2$, $R_3 = H$; $R_4$, $R_5 = CH_3$.

The following compound served as the starting material:

(a)
(5Z,13E)-(8R,9S,11R,12R,15S)-9,11,15-Tris(tetrahydropyran-2-yloxy)-19-methyl-5,13,18-prostatrienoic Acid Methyl Ester At 5°, 0.9 ml. of dihydropyran and 4 mg. of p-toluenesulfonic acid were added to a solution of 321 mg. of the methyl ester obtained according to Example 1(k) in 12 ml. of methylene chloride. The mixture was stirred for 30 minutes at 0°, introduced into 6 ml. of saturated sodium bicarbonate solution, diluted with ether, and the organic phase was shaken twice with water, dried over magnesium sulfate, and evaporated under vacuum. After filtration of the evaporation residue over silica gel, 453 mg. of the title compound was obtained with ether/hexane (1+1) as a colorless oil.

(b)
(5Z,13E)-(8R,9S,11R,12R,15S)-9,11,15-Tris(tetrahydropyran-2-yloxy)-19-methyl-5,13,18-prostatrien-1-ol To a suspension of 220 mg. of lithium aluminum hydride in 20 ml. of ether was added dropwise at 10° a solution of the 453 mg. of product prepared according to Example 23(a) in 20 ml. of ether. The mixture was stirred for 1.5 hours at room temperature. Excess lithium aluminum hydride was then destroyed by the dropwise addition of ethyl acetate, and 2 ml. of water was added to the mixture. The latter was stirred for 45 minutes at room temperature, filtered, and evaporated under vacuum. After filtration of the residue over silica gel, 400 mg. of the title compound was obtained with hexane/ether as a colorless oil.

(c) A mixture of 400 mg. of the prostatrien-1-ol obtained according to 23(b), 1.7 ml. of pyridine, and 0.7 ml. of acetic anhydride was allowed to stand at room temperature for 14 hours. After evaporation under vacuum, 430 mg. of the 1-acetate was obtained as a light-yellow oil. The thus-obtained 1-acetate was stirred for 4 hours at 50° with 10 ml. of a mixture of acetic acid/water/tetrahydrofuran (65/35/10), evaporated under vacuum, and the residue purified by column chromatography on silica gel. With ether/ethyl acetate (8+2), 190 mg. of the title compound was obtained as a colorless oil.

IR: 3400, 3000–2860, 1738, 1670, 1650, 1440, 1240, 1170, 1055, 1030 cm$^{-1}$.

EXAMPLE 24

(5Z,13E)-(8R,9S,11R,12R,15R)-1-Acetoxy-19-methyl-5,13,18-prostatriene-9,11,15-triol General Formula I: A=cis-CH=CH; B=trans-CH=CH;

$X\text{---}Y = -CH_2-\underline{CH}; Z = \phantom{x}\overline{\phantom{x}}\phantom{xx};$
$\phantom{xxxxxxxxxxxxxxxxx}\overline{\overline{OH}}\phantom{xx}\overline{O}H\phantom{xx}H$ $W = \phantom{x}\overline{\phantom{x}}C\text{---}; R_1 = -CH_2O-\underset{\underset{O}{\|}}{C}-CH_3;$
$\phantom{xxxxxxxx}H\phantom{xx}\overline{O}H$ $R_2$, $R_3 = H$; $R_4$, $R_5 = CH_3$.

The title compound was obtained, starting with the prostatrienoic methyl ester obtained according to Example 2(d), analogously to the directions described in Example 23.

IR: 3400, 3000–2850, 1737, 1670, 1650, 1440, 1240, 1170, 1055, 1025 cm$^{-1}$.

EXAMPLE 25

(5Z,13E)-(8R,11R,12R,15S)-1-Acetoxy-9-oxo-19-methyl-5,13,18-prostatriene-11,15-diol General Formula I: A=cis-CH=CH; B=trans-CH=CH;

$X\text{---}Y = -CH_2-\underline{CH}; Z = {>}C=O;$
$\phantom{xxxxxxxxxxxxxxxxx}\overline{\overline{OH}}$ $W = \phantom{x}\overline{\phantom{x}}C\text{---}; R_1 = -CH_2O-\underset{\underset{O}{\|}}{C}-CH_3;$
$\phantom{xxxxxxxx}\overline{O}H\phantom{xx}H$ $R_2$, $R_3 = H$; $R_4$, $R_5 = CH_3$.

At −45°, 1.2 ml. of N,N-diethyltrimethylsilylamine was added to a solution of 98 mg. of the 1-acetate produced according to Example 23 in 4 ml. of absolute acetone. The mixture was stirred for 6.5 hours at −40°. Thereafter, the mixture was diluted with 30 ml. of ether, previously cooled to −70°, shaken once with 5 ml. of ice-cold sodium bicarbonate solution and twice with respectively 5 ml. of saturated sodium chloride solution, dried with sodium sulfate, and evaporated under vacuum. The 11,15-bis(trimethylsilyl ether) obtained in this way was dissolved in 16 ml. of absolute methylene chloride and combined at +5° with a solution of 665 mg. of Collins reagent (preparation see Org. Syntheses 52:5), stirred for 10 minutes, diluted with 50 ml. of ether, filtered, and evaporated under vacuum. To split off the silyl ether blocking groups, the residue was stirred with a mixture of 9 ml. of methanol, 0.9 ml. of water, and 0.45 ml. of glacial acetic acid for 45 minutes at room temperature. The mixture was then diluted with 60 ml. of ether, shaken once with 10 ml. of sodium bicarbonate solution and twice with respectively 10 ml. of saturated sodium chloride solution, dried over magnesium sulfate, and evaporated under vacuum. After purification by preparative layer chromatography (ether/dioxane 9+1 as the eluent) on silica gel plates, 50 mg. of the title compound was obtained as a colorless oil.

IR: 3400, 3000–2860, 1740, 1730, 1670, 1650, 1440, 1160, 1070 cm$^{-1}$.

EXAMPLE 26

(5Z,13E)-(8R,11R,12R,15R)-1-Acetoxy-9-oxo-19-methyl-5,13,18-prostatriene-11,15-diol General Formula I: A=cis-CH=CH; B=trans-CH=CH;

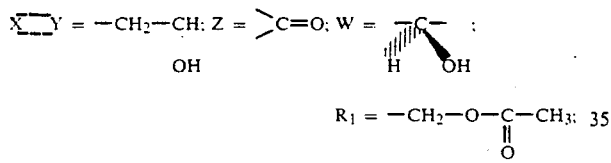

$R_1 = -CH_2-O-C-CH_3$; 
            ‖
            O $R_2, R_3 = H$; $R_4, R_5 = CH_3$.

Starting with the 1-acetate obtained according to Example 24, the title compound was obtained according to the directions given in Example 25.

EXAMPLE 27

(5Z,13E)-(8R,11R,12R,15S)-1-[(N-Methanesulfonyl)-carbamoyloxy]-9-oxo-19-methyl-5,13,18-prostatriene-11,15-diol General Formula I: A=cis-CH=CH; B=trans-CH=CH;

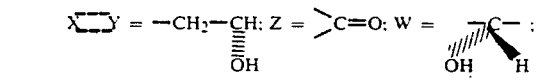

$R_1 = -CH_2-O-CO-NH-SO_2CH_3$; $R_2, R_3 = H$ $R_4, R_5 = CH_3$.

At 0°, 145 mg. of methanesylfonyl isocyanate was added to a solution of 304 mg. of the alcohol obtained according to Example 23(b) in 10 ml. of absolute toluene. The mixture was stirred for 1 hour at 20°–25°, combined with water, extracted with ether, the extract washed with saturated sodium chloride solution, dried over magnesium sulfate, and evaporated under vacuum. After filtration of the residue over silica gel with methylene chloride, 280 mg. of the 1-[(N-methanesulfonyl)-carbamoyloxy]-9,11,15-tris-THP ether was obtained. The further reaction steps to obtain the title compound follow the directions for the preparation of the compound of Example 25.

IR: 3400, 3000–2860, 1735 (shoulder), 1720, 1670, 1650, 1440, 1345, 1160, 1075 cm$^{-1}$.

EXAMPLE 28

(5Z,13E)-(8R,11R,12R,15R)-1-[(N-Methanesulfonyl)-carbamoyloxy]-9-oxo-19-methyl-5,13,18-prostatriene-11,15-diol General Formula I: A=cis-CH=CH; B=trans-CH=CH;

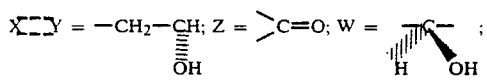

$R_1 = -CH_2-O-CO-NH-SO_2-CH_3$; $R_2, R_3 = H$; $R_4, R_5 = CH_3$.

Analogously to the directions given in Example 27, the title compound was obtained, starting with the 15-isomer to 23(b) obtained as the intermediate product during the preparation of the compound of Example 24.

IR: 3400, 3000–2860, 1735 (shoulder), 1720, 1670, 1650, 1440, 1345, 1160, 1075 cm$^{-1}$.

EXAMPLE 29

(5Z,10Z,13E)-(8R,12R,15RS)-15-Hydroxy-9-oxo-15,19-dimethyl-5,10,13,18-prostatetraenoic Acid and the Methyl Ester Thereof General Formula I: A=cis-CH=CH; B=trans-CH=CH;

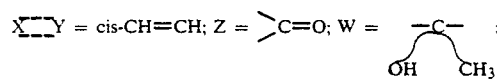

$R_1 = COOH, COOCH_3$; $R_2, R_3 = H$; $R_4, R_5 = CH_3$.

6.2 g. of the ketone obtained according to 1(g) was dissolved in 200 ml. of absolute tetrahydrofuran and gradually combined at −70° with 45 ml. of an ethereal methylmagnesium bromide solution (from 32.08 g. of magnesium filings, 73 ml. of methyl bromide, and 396 ml. of absolute ether). After stirring for another 15 minutes, the reaction solution was gradually combined with 500 ml. of ammonium chloride solution, and during this step the temperature rose to −15°. After another 15 minutes of agitation, the aqueous phase was extracted four times with ether. The combined organic phases were dried over magnesium sulfate, evaporated under vacuum, and purified by chromatography on silica gel with methylene chloride/1–5% ethanol, thus obtaining 5.7 g. of the 15-methyl alcohol, which was converted into the title compounds according to the directions in Examples 3 and 5, respectively.

IR: 3400, 3000–2850, 1735, 1700, 1670, 1650, 1590, 1440, 1170, 1040 cm$^{-1}$.

EXAMPLE 30

(5Z,13E)-(8R,11R,12R,15RS)-9-Oxo-11,15-dihydroxy-15,19-dimethyl-5,13,18-prostatrienoic Acid Methylsulfamide General Formula I: A=cis-CH=CH; B=trans-CH=CH;

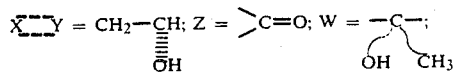

$R_1 = -CO-NH-SO_2-CH_3$; $R_2$, $R_3 = H$; $R_4$, $R_5 = CH_3$.

The title compound is prepared starting with the 15-methyl alcohol described in Example 29 analogously to the procedure disclosed in Examples 3(a), 3(b), 3(c), and 21.

IR: 3400, 3000–2860, 1735, 1720, 1670, 1650, 1435, 1340, 1165, 1070 cm$^{-1}$.

EXAMPLE 31

(5Z,10Z,13E)-(8R,12R,15S)-15-Hydroxy-9-oxo-16,16,19-trimethyl-5,10,13,18-prostatetraenoic Acid and the Methyl Ester Thereof General Formula I: A=cis-CH=CH; B=trans-CH=CH;

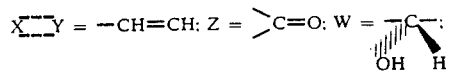

$R_1 = COOH$, $COOCH_3$; $R_2$, $R_3$, $R_4$, $R_5 = CH_3$.

The following compound served as the educt:

(a) 2,2,5-Trimethyl-4-hexenoic Acid Methyl Ester 300 g. of a 10% solution of lithium diisopropylamide in hexane was introduced into 90 ml. of absolute tetrahydrofuran, cooled to 0°, and combined dropwise under agitation with a solution of 28 g. of isobutyric acid methyl ester in 150 ml. of absolute tetrahydrofuran. The reaction solution was stirred for one hour at 0°, then cooled to −40° and subsequently added to a solution of 58 g. of 4-bromo-2-methyl-2-butene (dimethylallyl bromide) in 60 ml. of absolute dimethyl sulfoxide maintained at −20°. While allowing the temperature of the solution to rise to room temperature, the solution was stirred for 6 hours and then combined with saturated sodium chloride solution. The organic phase was separated, the aqueous phase was extracted five times with respectively 200 ml. of a 1/1 mixture of ether and hexane. The combined organic phases were washed neutral with 0.5N hydrochloric acid and saturated sodium chloride solution, dried over magnesium sulfate, and concentrated on a forced circulation evaporator. The residue was distilled under vacuum, thus obtaining 20.7 g. of the title compound, b.p. (13 mm.) 74°.

(b) (3,3,6-Trimethyl-2-oxo-5-heptenylidene)triphenylphosphorane 34.28 g. of triphenylmethylphosphonium bromide (dried for 4 hours at 40° on an oil pump) was suspended in 500 ml. of absolute ether and combined dropwise with 39 ml. of phenyllithium solution in benzene/ether. The reaction solution was agitated overnight at room temperature and under argon. Subsequently, 7.83 g. of the ester obtained according to (a), dissolved in 500 ml. of absolute ether, was added dropwise to the reaction mixture and the latter was agitated overnight at room temperature. Thereafter, the thus-produced precipitate was dissolved in water, the organic phase was separated and combined with the ether extracts of the aqueous phase which had been combined with sodium chloride.

The combined organic phases were washed with saturated sodium chloride solution, dried over magnesium sulfate, and evaporated on a forced circulation evaporator. The residue was purified by column chromatography on silica gel with ethyl acetate as the eluent, thus obtaining 9.4 g. of the desired compound. The further reaction steps took place according to the directions for the preparation of the compounds of Example 5 [via the stages analogously to Examples 1(g), 1(h), and 3].

IR: 3400, 3000–2850, 1735, 1700, 1670, 1650, 1590, 1440, 1170, 1050 cm$^{-1}$.

EXAMPLE 32

(5Z,13E)-(8R,11R,12R,15S)-9-Oxo-11,15-dihydroxy-16,16,19-trimethyl-5,13,18-prostatrienoic Acid Methylsulfamide General Formula I: A=cis-CH=CH; B=trans-CH=CH;

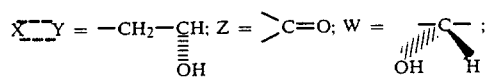

$R_1 = -CO-NH-SO_2-CH_3$; $R_2$, $R_3$, $R_4$, $R_5 = CH_3$.

The educt was the 3′S-(tetrahydropyran-2-yloxy) isomer obtained during the preparation of the compound of Example 31 and synthesized according to the directions in 3(c). The further reaction steps followed the description of Example 21.

IR: 3400, 3000–2860, 1735, 1720, 1670, 1650, 1440, 1340, 1160, 1070 cm$^{-1}$.

EXAMPLE 33

(5Z,13E)-(8R,11R,12R,15S)-9-Oxo-11,15-dihydroxy-16,16,19-trimethyl-5,13,18-prostatrienoic Acid Acetylamide General Formula I: A=cis-CH=CH; B=trans-CH=CH;

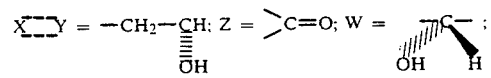

$R_1 = -CO-NH-CO-CH_3$; $R_2$, $R_3$, $R_4$, $R_5 = CH_3$.

The educt employed was the (5Z,13E)-(8R,11R,12R,15S)-9-oxo-16,16,19-trimethyl-11,15-bis(-tetrahydropyran-2-yloxy)-5,13,18-prostatrienoic acid obtained during the preparation of the compound of Example 31 as the intermediate product (after the Jones oxidation)—analogously to the directions for Example 3(e). 224 mg. of this acid was added, together with 60 mg. of triethylamine, to 5 ml. of acetonitrile and combined at 0° with 44 mg. of acetylisocyanate in 5 ml. of acetonitrile. The reaction mixture was stirred for 2 hours under argon at room temperature. After removal of the solvent by means of a forced circulation evaporator, the residue was brought to pH 6 with 10% strength sulfuric acid and extracted with ether. The organic phase was washed with saturated sodium chloride solution, dried over magnesium sulfate, and evaporated under vacuum, thus obtaining 210 mg. of the desired 11,15-di-(tetrahydropyranyl)-ether acetylamide which was used without further purification in the THP ether splitting reaction analogously to the directions for Example 3(f) to produce the title compound.

IR: 3400, 3000–2860, 1735 (wide), 1703, 1670, 1650, 1440, 1160, 1075 cm$^{-1}$.

EXAMPLE 34

(5Z,10Z,13E,18Z)-(8R,12R,15RS)-19-Chloro-15-hydroxy-9-oxo-15-methyl-5,10,13,18-prostatetraenoic Acid and the Methyl Ester Thereof General Formula I: A=cis-CH=CH; B=trans-CH=CH;

$$X\text{---}Y = \text{cis-CH=CH}; \quad Z = {>}C{=}O; \quad W = -\underset{\underset{CH_3}{OH}}{C}-;$$

$R_1$=COOH, COOCH$_3$; $R_2$, $R_3$=H; $R_4$=CH$_3$; $R_5$—Cl.

(a) 3-Chloro-2-butenylmalonic Acid Ethyl Ester

A three-necked flask equipped with agitator, reflux condenser, and dropping funnel was charged with 11.5 g. of sodium, cut into small pieces. Then, 250 ml. of absolute ethanol was added dropwise so quickly that the solution was boiling vigorously. Thereafter, 80 g. of distilled malonic acid diethyl ester was added dropwise to the hot alcoholate solution. After allowing the solution to cool to about 75°, the reaction solution was combined dropwise with 66 g. of cis,trans-1,3-dichloro-2-butene, thus assuming a yellow coloring. After one hour of agitation under heating, the suspension, exhibiting a pH of 5–6 and at that point in time having been almost completely decolorized, was freed of the precipitated sodium chloride by filtration. The filtrate was concentrated and combined with the methylene chloride obtained by washing the precipitate. The organic solution was then shaken with saturated sodium chloride solution, dried over magnesium sulfate, concentrated on a forced circulation evaporator, and fractionated under vacuum, thus obtaining 76 g. of the title compound, b.p. 100°–108° (0.5 mm.) and 76°–78° (0.1 mm.), respectively.

(b) [(2Z)-3-Chloro-2-butenyl]-malonic Acid 24.87 g. of diester was heated under reflux for 3.5 hours together with 19.6 g. of potassium hydroxide in 50 ml. of ethanol and 25 ml. of water. After withdrawing the solvent under vacuum, the residue was dissolved in 25 ml. of water and combined dropwise under ice cooling with concentrated hydrochloric acid to pH 1. Subsequently, the aqueous phase was extracted five times with respectively 100 ml. of ether. The combined ether extracts were washed with a small amount of saturated sodium chloride solution, dried over sodium sulfate, and concentrated to dryness under vacuum. The residue was recrystallized from benzene, thus obtaining 15.2 g. of final product, m.p. 95°–97°.

(c) (4Z)-5-Chloro-4-hexenoic Acid 15 g. of the dicarboxylic acid obtained in the preceding reaction stage was heated in a distillation apparatus for 3 hours to 150°; during this step, carbon dioxide was liberated. The product was then distilled under vacuum, and 10.8 g. of final product was isolated, b.p. 129°–130° (13 mm.).

(d) (4Z)-5-Chloro-4-hexenoic Acid Methyl Ester

A solution of 10.4 g. of the carboxylic acid prepared according to (c) in 50 ml. of ether was combined with such an amount of ethereal diazomethane solution that there was no longer any liberation of nitrogen during the addition of the reagent and the yellow coloring of the reaction solution remained. Excess diazomethane and solvent were then removed under vacuum, and the residue was distilled with the aid of a water jet aspirator, thus obtaining 10.6 g. of final product, b.p. 87°–89° (18 mm.).

(e) [(5Z)-6-Chloro-2-oxo-5-heptenylidene]triphenylphosphorane 96.7 g. of triphenylmethylphosphonium bromide (dried for 4 hours at 40° on an oil pump) was suspended in 500 ml. of absolute ether and combined dropwise under cooling with 125 ml. of phenyllithium solution in benzene/ether. The reaction solution was stirred overnight at room temperature and under argon. Subsequently, a solution of 21.43 g. of the methyl ester obtained in the preceding reaction stage in 500 ml. of absolute ether was added dropwise to the ylene solution. The reaction mixture was stirred overnight at room temperature. Thereafter, the precipitate was dissolved in water, the organic phase was separated, and the aqueous phase, after adding sodium chloride, was repeatedly extracted with ether. The combined organic phases were washed with saturated sodium chloride solution, dried over magnesium sulfate, and evaporated under vacuum. The residue was purified by column chromatography on silica gel with ethyl acetate/0–90% isopropanol as the eluent, thus producing 43.15 g. of the desired compound; m.p. 109°–113° (ethyl acetate). The further reaction steps were conducted analogously to the directions for the preparation of the compound of Example 29 [via stages 1(g), 3, and 5].

IR: 3400, 3000–2860, 1737, 1700, 1670, 1650, 1590, 1440, 1170, 1040 cm$^{-1}$.

EXAMPLE 35

(5Z,13E,18Z)-(8R,12R,15RS)-19-Chloro-9-oxo-11,15-dihydroxy-15-methyl-5,13,18-prostatrienoic Acid Methylsulfamide General Formula I: A=cis-CH=CH; B=trans-CH=CH;

$$X\text{---}Y = -CH_2-\underset{\underset{OH}{\equiv}}{CH}; \quad Z = {>}C{=}O; \quad W = -\underset{\underset{CH_3}{OH}}{C}-;$$

$R_1$=—CO—NH—SO$_2$—CH$_3$; $R_2$, $R_3$=H; $R_4$=CH$_3$; $R_5$=Cl.

The title compound was prepared analogously to the directions given in Examples 3(a), 3(b), 3(c), and 21. In this case, the educt employed was the 15-methyl-15-alcohol synthesized according to the description in Example 29 by Grignard reaction of the 15-ketone obtained after the first Wittig condensation (and already required as the intermediate in Example 34).

IR: 3400, 3000–2860, 1735, 1720, 1670, 1650, 1435, 1340, 1165, 1065 cm$^{-1}$.

EXAMPLE 36

(5Z,10Z,13E,18Z)-(8R,12R,15S)-19-Chloro-15-hydroxy-9-oxo-16,16-dimethyl-5,10,13,18-prostatetraenoic Acid and the Methyl Ester Thereof General Formula I: A=cis-CH=CH; B=trans-CH=CH;

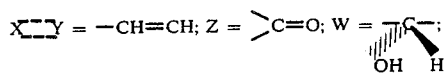

$R_1$=COOH, COOCH$_3$; $R_2$, $R_3$, $R_4$=CH$_3$; $R_5$=Cl.

The methyl ester of 5-chloro-2,2-dimethyl-4-hexenoic acid, obtained by the condensation of isobutyric acid methyl ester with 1,3-dichloro-2-butene analogously to the directions given in Example 31(a) was prepared in accordance with Examples 31(b) and 5 [via the stages analogously to Examples 1(g), 1(h), and 3].

IR: 3400, 3000-2860, 1737, 1700, 1670, 1650, 1590, 1440, 1170, 1060 cm$^{-1}$.

EXAMPLE 37

(5Z,13E,18Z)-(8R,11R,12R,15S)-19-Chloro-11,15-dihydroxy-9-oxo-16,16-dimethyl-5,13,18-prostatrienoic Acid Methylsulfamide General Formula I: A=cis-CH=CH; B=trans-CH=CH;

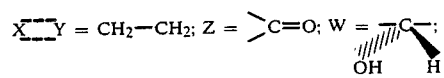

$R_1$=—CO—NH—SO$_2$—CH$_3$; $R_2$, $R_3$, $R_4$=CH$_3$; $R_5$=Cl.

Starting with the 3'S-(tetrahydropyran-2-yloxy) isomer obtained in Example 36 and prepared analogously to the directions of Example 3(c), the title compound was synthesized according to the directions given in Example 21.

IR: 3400, 3000-2860, 1735, 1720, 1670, 1650, 1440, 1340, 1160, 1065 cm$^{-1}$.

EXAMPLE 38

(5Z,13E,18Z)-(8R,11R,12R,15S)-19-Chloro-11,15-dihydroxy-9-oxo-16,16-dimethyl-5,13,18-prostatrienoic Acid Acetylamide General Formula I: A=cis-CH=CH; B=trans-CH=CH;

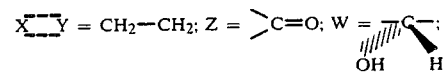

$R_1$=—CO—NH—CO—CH$_3$; $R_2$, $R_3$, $R_4$=CH$_3$; $R_5$=Cl.

Starting with the prostatrienoic acid obtained during the preparation of the compound of Example 36 as the intermediate (after the Jones oxidation)—analogously to the directions in Example 3(c)—the title compound was obtained by following the procedure of Example 33.

IR: 3400, 3000-2850, 1735 (wide), 1703, 1670, 1650, 1440, 1160, 1070 cm$^{-1}$.

EXAMPLE 39

(5Z,13E)-(8R,9S,11R,12R,15S)-9,11,15-Trihydroxy-19-methyl-5,13,18-prostatrienoic Acid (4-Phenyl)-phenacyl Ester General Formula I: A=cis-CH=CH; B=trans-CH=CH;

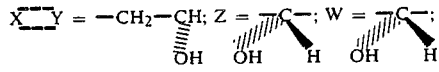

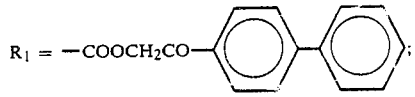

$R_2$, $R_3$=H; $R_4$, $R_5$=CH$_3$.

Under argon, 66 mg. of the prostatrienoic acid obtained according to Example 1(j) was agitated for 14 hours at room temperature with 21 mg. of triethylamine and 53 mg. of p-phenylphenacyl bromide in 4 ml. of acetone. After dilution with water, the mixture was extracted with ether, the ether extract was washed with saturated sodium chloride solution, dried over magnesium sulfate, and evaporated under vacuum. The residue was purified by chromatography on silica gel (methylene chloride/1-5% isopropanol), thus obtaining 52 mg. of the title compound.

IR: 3500-3400, 3000-2860, 1735, 1670, 1650, 1440, 1175, 1050, 980 cm$^{-1}$.

Analogously to Example 39, it is also possible to convert all other prostaglandin acids described in the preceding examples into the corresponding phenacyl esters.

EXAMPLE 40

Tris(hydroxymethyl)aminomethane Salt of (5Z,13E)-(8R,9S,11R,12R,15S)-9,11,15-Trihydroxy-19-methyl-5,13,18-prostatrienoic Acid General Formula I: A=cis-CH=CH; B=trans-CH=CH;

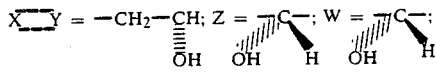

$R_1$=—COONH$_3$C(CH$_2$OH)$_3$; $R_2$, $R_3$=H; $R_4$, $R_5$=CH$_3$.

At 60°, a solution of 91 mg. of the prostatrienoic acid obtained according to Example 1(j) in 14 ml. of acetonitrile was combined with a solution of 32.9 mg. of tris(hydroxymethyl)aminomethane in 0.1 ml. of water. The mixture was allowed to stand for 14 hours at room temperature, thus obtaining 65 mg. of the title compound.

Analogously to Example 40, it is also possible to convert all other prostaglandin acids described in the preceding examples into the corresponding tris(hydroxymethyl)aminomethane salts.

EXAMPLE 41

(5Z,13E)-(8R,9S,11R,12R,15RS)-9,11,15-Trihydroxy-15,19-dimethyl-5,13,18-prostatrienoic Acid Methyl Ester

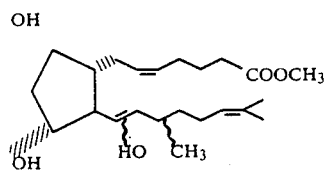

General Formula I: A=cis CH=CH; B=trans CH=CH;

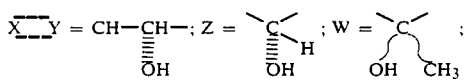

$R_1$=COOCH$_3$; $R_1R_3$=H; $R_4$, $R_5$, =CH$_3$.

(a) (1S,5R,6R,7R,3'RS)-7-Benzoyloxy-6-[(E)-3-hydroxy-3,7-dimethyl-1,6-octadienyl]-2-oxabicyclo[3.3.0]octan-3-one

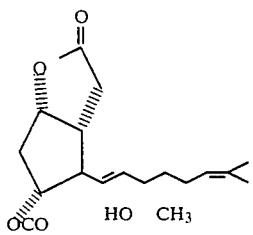

A solution of 3 g. of the ketone obtained according to Example 1(g) in 110 ml. of absolute tetrahydrofuran was cooled to −70° C. and combined dropwise under argon with 25 ml. of an ethereal methylmagnesium bromide solution, so that the temperature did not rise above −60° C. After one hour, the reaction mixture was poured into 100 ml. of saturated ammonium chloride solution, stirred for 10 minutes, and then such an amount of water was added that the precipitate redissolved. The aqueous phase was then extracted four times with 200 ml. of ether; the combined organic phases were washed with saturated sodium chloride solution, dried over magnesium sulfate, and concentrated to dryness under vacuum. The residue was purified by column chromatography on silica gel with toluene/0-25% ethyl acetate as the eluent, thus obtaining 2.46 g. of the title compound.

(b) (2RS,3aR,4R,5R,6aS)-4-[(E)-(3RS)-3-Hydroxy-3,7-dimethyl-1,6-octadienyl]perhydrocyclopenta[b]furan-2,5-diol

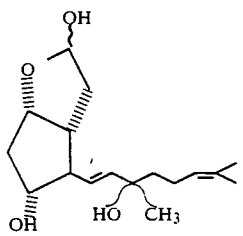

A solution of 570 mg. of the lactone obtained in the preceding reaction stage in 20 ml. of absolute toluene was combined dropwise under argon at a temperature of −60° C. with 6.2 ml. of a 20% DIBAH solution in toluene. After a further period of agitation for 30 minutes at this temperature, the reaction was terminated by the dropwise addition of 2.5 ml. of isopropanol and—after allowing the temperature to rise to 0° C.—of 25 ml. of water. The mixture was stirred for another 10 minutes at 0° C., the residue was filtered off and then washed with a large amount of methylene chloride. The combined organic phases were washed with saturated sodium chloride solution, dried over sodium sulfate, and concentrated to dryness under vacuum. The amount of 426 mg. of product, obtained as a residue, was utilized without further purification in the subsequent reaction stage.

(c) (5Z,13E)-(8R,9S,11R,12R,15RS)-9,11,15-Trihydroxy-15,19-dimethyl-5,13,18-prostatrienoic Acid

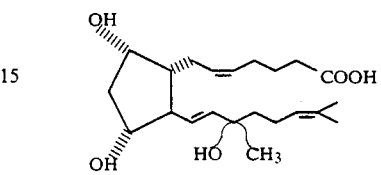

16.48 ml. of a solution of methanesulfinylmethyl sodium in absolute dimethyl sulfoxide (solution: 2 g. of 50% sodium hydride suspension was stirred in 40 ml. of absolute dimethyl sulfoxide for one-half hour at 65°-70° C.) was added dropwise to a solution of 3.8 g. of 4-carboxybutyltriphenylphosphonium bromide in 10 ml. of absolute dimethyl sulfoxide; the mixture was stirred for 30 minutes at room temperature. This ylene solution was then added dropwise within 15 minutes to a solution of the 426 mg. of lactol obtained in the preceding reaction stage in 10 ml. absolute dimethyl sulfoxide, and the mixture was then stirred at 35° C. for 4 hours. Thereafter 75 ml. of ice water was added to the reaction solution and extracted three times with ether. The aqueous phase was adjusted to pH 4 with citric acid solution, combined with sodium chloride, and extracted five times in succession with a mixture of ether/hexane=1/1 and three times with methylene chloride. The ether/hexane extract was dried, evaporated under vacuum, and the residue of the evaporation was purified by column chromatography on silica gel with ethyl acetate/0–10% isopropanol, thus obtaining 161 mg. of the title compound.

(d) 116 mg. of the acid obtained in the preceding reaction stage was—dissolved in ether—combined with a quantity of ethereal diazomethane solution until the yellow coloring of the reaction solution remained permanently. The excess diazomethane was removed under vacuum at room temperature. The compound was purified by column chromatography on silica gel with ethyl acetate as the eluent, thus obtaining 86 mg. of (5Z,13E)-(8R,9S,11R,12R,15RS)-9,11,15-trihydroxy-15,19-dimethyl-5,13,18-prostatrienoic acid methyl ester.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

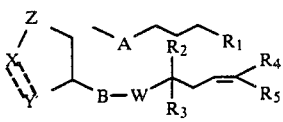

wherein $R_1$ is

wherein $R_6$ is hydroxy, a straight chain or branched alkoxy of 1–10 carbon atoms; aryloxy; O—$CH_2$—U—V wherein U is a direct bond, carbonyl or carbonyloxy and V is a phenyl ring substituted by one or more of phenyl, alkoxy of 1–2 carbon atoms, or halogen atoms, A is —$CH_2$—$CH_2$— or cis- or trans-CH=CH—; B is —$CH_2$—$CH_2$—, trans-CH=CH— or C≡C or

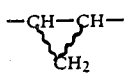

wherein the methylene group can be the α- or β-position; W is free or functionally modified hydroxymethylene, a free or functionally modified carbonyl, or

wherein $R_{11}$ is alkyl of 1–5 carbon atoms and the OH-group can be in the α- or β-position and can be functionally modified; Z is carbonyl which can be free or functionally modified; X⎯⎯⎯Y is

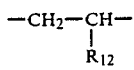

wherein $R_{12}$ is a cyanide group (—CN); $R_2$ is a hydrogen atom or $C_{1-5}$-alkyl; $R_3$ is a hydrogen atom or $C_{1-5}$-alkyl; $R_4$ and $R_5$ each are methyl; and, when $R_6$ is hydroxy, the physiologically acceptable salts thereof with bases; wherein "functionally modified" OH refers to OH etherified by tetrahydropyranyl, tetrahydrofuranyl, α-ethoxyethyl, trimethylsilyl, dimethyl-tert-butylsilyl or tri-p-benzylsilyl or esterified by the acyl group of a $C_{1-15}$ organic carboxylic or sulfonic acid; and "functionally modified" carbonyl refers to carbonyl converted to a cyclic ketal with ethylene glycol, 1,3-propanediol, 2,2-dimethyl-1,3-propanediol, 1,2-cyclopentanediol, or glycerol.

2. A compound of the formula

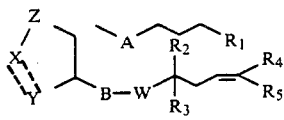

wherein $R_1$ is

wherein $R_6$ is hydroxy, a straight chain or branched alkoxy of 1–10 carbon atoms; aryloxy; O—$CH_2$—U—V wherein U is a direct bond, carbonyl or carbonyloxy and V is a phenyl ring substituted by one or more of phenyl, alkoxy of 1–2 carbon atoms, or halogen atoms, preferably bromine atoms; A is —$CH_2$—$CH_2$— or cis- or trans-CH=CH—; B is —$CH_2$—$CH_2$—, trans-CH=CH— or —C≡C— or

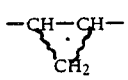

wherein the methylene group can be in the α- or β-position; W is free or functionally modified hydroxymethylene, a free or functionally modified carbonyl, or

wherein $R_{11}$ is alkyl of 1–5 carbon atoms and the OH-group can be in the α- or β-position and can be functionally modified; Z is hydroxymethylene; which can be free or functionally modified; X⎯⎯⎯Y is

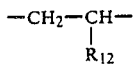

wherein $R_{12}$ is a cyanide group (—CN), or a free or functionally modified hydroxy; $R_2$ is a hydrogen atom or $C_{1-5}$ alkyl; $R_3$ is a hydrogen atom or $C_{1-5}$ alkyl; $R_4$ and $R_5$ each are methyl; and, when $R_6$ is hydroxy, the physiologically acceptable salts thereof with bases; wherein "functionally modified" OH refers to OH etherified by tetrahydropyranyl, tetrahydrofuranyl, α-ethoxyethyl, trimethylsilyl, dimethyl-tert-butylsilyl or tri-p-benzylsilyl or esterified by the acyl group of a $C_{1-15}$ organic carboxylic or sulfonic acid; and "functionally modified" carbonyl refers to carbonyl converted to a cyclic ketal with ethylene glycol, 1,3-propanediol, 2,2-dimethyl-1,3-propanediol, 1,2-cyclopentanediol, or glycerol.

3. A compound of the formula

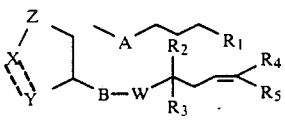

wherein $R_1$ is

wherein $R_6$ is hydroxy, a straight chain or branched alkoxy of 1–10 carbon atoms; aryloxy; O—$CH_2$—U—V wherein U is a direct bond, carbonyl or carbonyloxy and V is a phenyl ring substituted by one or more of phenyl, alkoxy of 1–2 carbon atoms, or halogen atoms, A is —CH₂—CH₂— or cis- or trans-CH=CH—; B is —CH₂—CH₂—, trans-CH=CH— or —C≡C— or

wherein the methylene group can be in the α- or β-position; W is free or functionally modified hydroxymethylene, a free or functionally modified carbonyl, or

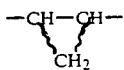

wherein R₁₁ is alkyl of 1-5 carbon atoms and the OH-group can be in the α- or β-position and can be functionally modified; Z is carbonyl which can be free or functionally modified; X⎯⎯⎯Y is —CH=CH—; R₂ is a hydrogen atom or C₁₋₅-alkyl; R₃ is a hydrogen atom or C₁₋₅-alkyl; R₄ and R₅ each are methyl; and when R₆ is hydroxy, the physiologically acceptable salts thereof with bases; wherein "functionally modified" OH refers to OH etherified by "tetrahydropyranyl, tetrahydrofuranyl, α-ethoxyethyl, trimethylsilyl, dimethyl-tert-butylsilyl or tri-p-benzylsilyl or esterified by the acyl group of a C₁₋₁₅ organic carboxylic or sulfonic acid; and "functionally modified" carbonyl refers to carbonyl converted to a cyclic ketal with ethylene glycol, 1,3-propanediol, 2,2-dimethyl-1,3-propanediol, 1,2-cyclopentanediol, or glycerol.

4. A compound of the formula

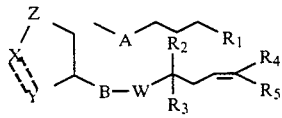

wherein R₁ is

wherein R₆ is hydroxy, a straight chain or branched alkoxy of 1-10 carbon atoms; aryloxy; O—CH₂—U—V wherein U is a direct bond, carbonyl or carbonyloxy and V is a phenyl ring substituted by one or more of phenyl, alkoxy of 1-2 carbon atoms, or halogen atoms, A is —CH₂—CH₂— and B is —CH₂—CH₂—, trans-CH=CH— or —C≡C— or

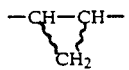

wherein the methylene group can be in the α- or β-position; or A is cis or trans-CH=CH— and B is —CH₂—CH₂— or

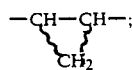

W is free or functionally modified hydroxymethylene, a free or functionally modified carbonyl, or

wherein R₁₁ is alkyl of 1-5 carbon atoms and the OH-group can be in the α- or β-position and can be functionally modified; Z is carbonyl or hydroxymethylene, either of which can be free or functionally modified; X⎯⎯⎯Y is either

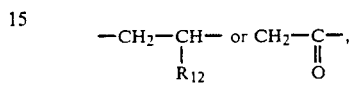

when Z is a free or functionally modified hydroxymethylene group, or is either

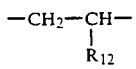

or —CH=CH—, when Z is a free or functionally modified carbonyl group, wherein R₁₂ is a cyanide group (—CN), or a free or functionally modified hydroxy; R₂ is a hydrogen atom or C₁₋₅-alkyl; R₃ is a hydrogen atom or C₁₋₅-alkyl; R₄ and R₅ each are methyl or one of R₄ and R₅ is a chlorine atom and the other is methyl; and, when R₆ is hydroxy, the physiologically acceptable salts thereof with bases; wherein "functionally modified" OH refers to OH etherified by tetrahydropyranyl, tetahydrofuranyl, α-ethoxyethyl, trimethylsilyl, dimethyl-tert-butylsilyl or tri-p-benzylsilyl or esterified by the acyl group of a C₁₋₁₅ organic carboxylic or sulfonic acid; and "functionally modified" carbonyl refers to carbonyl converted to a cyclic ketal with ethylene glycol, 1,3-propanediol, 2,2-dimethyl-1,3-propanediol, 1,2-cyclopentanediol, or glycerol.

5. A compound of claim 2 wherein R₁₂ is OH.

6. A compound of claim 1 wherein R₆ is hydroxy or alkoxy.

7. A compound of claim 4 wherein both R₄ and R₅ are CH₃.

8. A compound of claim 2, wherein R₆ is hydroxy or alkoxy.

9. A compound of claim 3, wherein R₆ is hydroxy or alkoxy.

10. A compound of claim 4, wherein R₆ is hydroxy or alkoxy.

11. (5Z,13E)-(8R,9S,11R,12R,15S)-9,11,15-Trihydroxy-19-methyl-5,13,18-prostatrienoic acid or its methyl ester, a compound of claim 2.

12. (5Z,13E)-(8R,9S,11R,12R,15R)-9,11,15-Trihydroxy-19-methyl-5,13,18-prostatrienoic acid or its methyl ester, a compound of claim 2.

13. (5Z,10Z,13E)-(8R,12R,15S)-15-Hydroxy-9-oxo-19-methyl-5,10,13,18-prostatetranoic acid or its methyl ester, a compound of claim 3.

14. (5Z,10Z,13E)-(8R,12R,15R)-15-Hydroxy-9-oxo-19-methyl-5,10,13,18-prostateraenoic acid or its methyl ester, a compound of claim 3.

15. (5Z,13E)-(8R,9S,11R,12R,15RS)-9,11,15-Trihydroxy-15,19-dimethyl-5,13,18-prostatrienoic acid methyl ester, a compound of claim 2.

16. (5Z,13E)-(8R,9S,11R,12R,15RS)-9,11,15-trihydroxy-15,19-dimethyl-5,13,18-prostatrienoic acid, a compound of claim 2.

17. (13E)-(8R,9S,11R,12R,15S)-9,11,15-Trihydroxy-19-methyl-13,18-prostadienoic acid or its methyl ester, a compound of claim 2.

18. (13E)-(8R,9S,11R,12R,15R)-9,11,15-Trihydroxy-19-methyl-13,18-prostadienoic acid or its methyl ester, a compound of claim 2.

19. (13E)-(8R,11R,12R,15S)-9-Oxo-11,15-dihydroxy-19-methyl-13,18-prostadienoic acid methyl ester, a compound of claim 4.

20. (13E)-(8R,11R,12R,15R)-9-Oxo-11,15-dihydroxy-19-methyl-13,18-prostadienoic acid methyl ester, a compound of claim 4.

21. (8R,9S,11R,12R,15S)-9,11,15-Trihydroxy-19-methyl-18-prostenoic acid or its methyl ester, a compound of claim 2.

22. (8R,9S,11R,12R,15R)-9,11,15-Trihydroxy-19-methyl-18-prostenoic acid or its methyl ester, a compound of claim 2.

23. (8R,11R,12R,15S)-9-Oxo-11,15-dihydroxy-19-methyl-18-prostenoic acid or its methyl ester, a compound of claim 4.

24. (8R,11R,12R,15R)-9-Oxo-11,15-dihydroxy-19-methyl-18-prostenoic acid or its methyl ester, a compound of claim 4.

25. (5Z,10Z,13E)-(8R,12R,15RS)-15-Hydroxy-9-oxo-15,19-dimethyl-5,10,13,18-prostatetraenoic acid or its methyl ester, a compound of claim 3.

26. (5Z,10Z,13E)-(8R,12R,15S)-15-Hydroxy-S-oxo-16,16,19-trimethyl-5,10,13,18-prostatetraenoic acid or its methyl ester, a compound of claim 3.

27. (5Z,13E)-8R,9S,11R,12R,15S)-9,11,15-Trihydroxy-19-methyl-5,13,18-prostatrieonic acid (4-phenyl)-phenacyl ester, a compound of claim 2.

28. Tris(hydroxymethyl)aminomethane salt of (5Z,13E)-(8R,9S,11R,12R,15S)-9,11,15-Trihydroxy-19-methyl-5,13,18-prostatrienoic acid, a compound of claim 2.

29. A pharmaceutical composition comprising an abortion-inducing effective amount per unit dosage of a compound of claim 1, in admixture with a pharmaceutically acceptable carrier.

30. A method of inducing abortion in a pregnant mammal which comprises administering thereto an amount of a compound of claim 1 effective to induce abortion.

31. (5Z,13E)-(8R,11R,12R,15S)-11-Cyano-15-hydroxy 9-oxo-19-methyl-5,13,18-prostatrienoic acid or its methyl ester, a compound of claim 1.

32. (5Z,13E)-(8R,11R,12R,15R)-11-Cyano-15-hydroxy-9-oxo-19-methyl-5,13,18-prostatrienoic acid or its methyl ester, a compound of claim 1.

33. A pharmaceutical composition comprising an abortion-inducing effective amount per unit dosage of a compound of claim 2, in admixture with a pharmaceutically acceptable carrier.

34. A pharmaceutical composition comprising an abortion-inducing effective amount per unit dosage of a compound of claim 3, in admixture with a pharmaceutically acceptable carrier.

35. A pharmaceutical composition comprising an abortion-inducing effective amount per unit dosage of a compound of claim 4, in admixture with a pharmaceutically acceptable carrier.

36. A method of inducing abortion in a pregnant mammal which comprises administering thereto an amount of a compound of claim 2 effective to induce abortion.

37. A method of inducing abortion in a pregnant mammal which comprises administering thereto an amount of a compound of claim 3 effective to induce abortion.

38. A method of inducing abortion in a pregnant mammal which comprises administering thereto an amount of a compound of claim 4 effective to induce abortion.

* * * * *